(12) United States Patent
Summer

(10) Patent No.: US 9,636,250 B2
(45) Date of Patent: May 2, 2017

(54) TONGUE GRASPING AND RESTRAINING APPARATUS AND METHODS

(76) Inventor: John D. Summer, Portland, OR (US)

(*) Notice: Subject to any disclaimer, the term of this patent is extended or adjusted under 35 U.S.C. 154(b) by 1467 days.

(21) Appl. No.: 11/986,044

(22) PCT Filed: May 18, 2006

(86) PCT No.: PCT/US2006/019759
§ 371 (c)(1),
(2), (4) Date: Nov. 17, 2007

(87) PCT Pub. No.: WO2006/125216
PCT Pub. Date: Nov. 23, 2006

(65) Prior Publication Data
US 2009/0126742 A1    May 21, 2009

Related U.S. Application Data

(60) Provisional application No. 60/684,849, filed on May 19, 2005, provisional application No. 60/720,650, (Continued)

(51) Int. Cl.
*A61F 5/56* (2006.01)
*A61C 7/36* (2006.01)

(52) U.S. Cl.
CPC ............. *A61F 5/566* (2013.01); *A61C 7/36* (2013.01)

(58) Field of Classification Search
CPC ...... A61F 5/56; A61F 5/566; A61F 2005/563; A61C 7/06; A61C 5/14; A61C 7/08; A63B 71/085; A61B 13/00
(Continued)

(56) References Cited

U.S. PATENT DOCUMENTS 4,198,967 A    4/1980    Dror
4,505,672 A    3/1985    Kurz
(Continued)

FOREIGN PATENT DOCUMENTS

WO    WO 2006/125216    11/2006

OTHER PUBLICATIONS

International Search Report dated Sep. 28, 2007, issued by the International Searching Authority in corresponding PCT Application No. PCT/US06/019759, filed May 18, 2006.
(Continued)

*Primary Examiner* — Victoria J Hicks
(74) *Attorney, Agent, or Firm* — Klarquist Sparkman, LLP

(57) ABSTRACT

A tongue grasping and restraining device holds the tongue securely during sleep in order to minimize the risk of the tongue slipping back and blocking the throat, a condition known as obstructive sleep apnea. Plural tongue gripping projections are coupled to upper and lower supports. The projections engage and hold the tongue. The upper and lower supports are biased toward one another into a tongue engaging position. The upper support is coupled to the user's upper jaw, for example, to a denture, dental appliance or by upper teeth engaging mechanisms. The lower support can be hinged or otherwise joined to the upper support or can be separate therefrom. A tube and rod mechanism in one embodiment couples the upper and lower supports together. Exemplary methods of manufacturing tongue gripping projections are also disclosed.

22 Claims, 10 Drawing Sheets

Related U.S. Application Data filed on Sep. 27, 2005, provisional application No. 60/758,603, filed on Jan. 13, 2006.

(58) Field of Classification Search
USPC .... 128/860, 859, 848, 845; 433/140, 19, 18, 433/21, 6; D24/180; 600/902
See application file for complete search history.

(56) References Cited

U.S. PATENT DOCUMENTS

| | | | |
|---|---|---|---|
| 4,676,240 A | 6/1987 | Gardy | |
| 4,884,581 A * | 12/1989 | Rescigno | A61B 13/00 |
| | | | 128/869 |
| 4,969,822 A | 11/1990 | Summer | |
| 5,066,226 A | 11/1991 | Summer | |
| 5,176,618 A | 1/1993 | Freedman | |
| 5,373,859 A | 12/1994 | Forney | |
| 5,465,734 A | 11/1995 | Alvarez et al. | |
| 5,592,951 A * | 1/1997 | Castagnaro et al. | 128/848 |
| 5,649,540 A | 7/1997 | Alvarez et al. | |
| 5,715,840 A * | 2/1998 | Hall | 128/848 |
| 5,915,385 A | 6/1999 | Hakimi | |
| 5,964,588 A * | 10/1999 | Cleary | 433/19 |
| 6,109,265 A * | 8/2000 | Frantz | A61F 5/566 |
| | | | 128/848 |
| 6,241,521 B1 * | 6/2001 | Garrison | 433/140 |
| 6,837,246 B1 | 1/2005 | DeLuke | |
| 6,955,172 B2 | 10/2005 | Nelson et al. | |
| 7,451,767 B2 * | 11/2008 | Keropian | 128/848 |
| 2003/0190575 A1 * | 10/2003 | Hilliard | 433/6 |
| 2008/0188947 A1 | 8/2008 | Sanders | |
| 2011/0178439 A1 | 7/2011 | Irwin et al. | |
| 2011/0226264 A1 | 9/2011 | Friedman et al. | |
| 2012/0138071 A1 | 6/2012 | Summer | |

OTHER PUBLICATIONS

Written Opinion dated Sep. 28, 2007, issued by the International Searching Authority in corresponding PCT Application No. PCT/US06/019759, filed May 18, 2006.

* cited by examiner

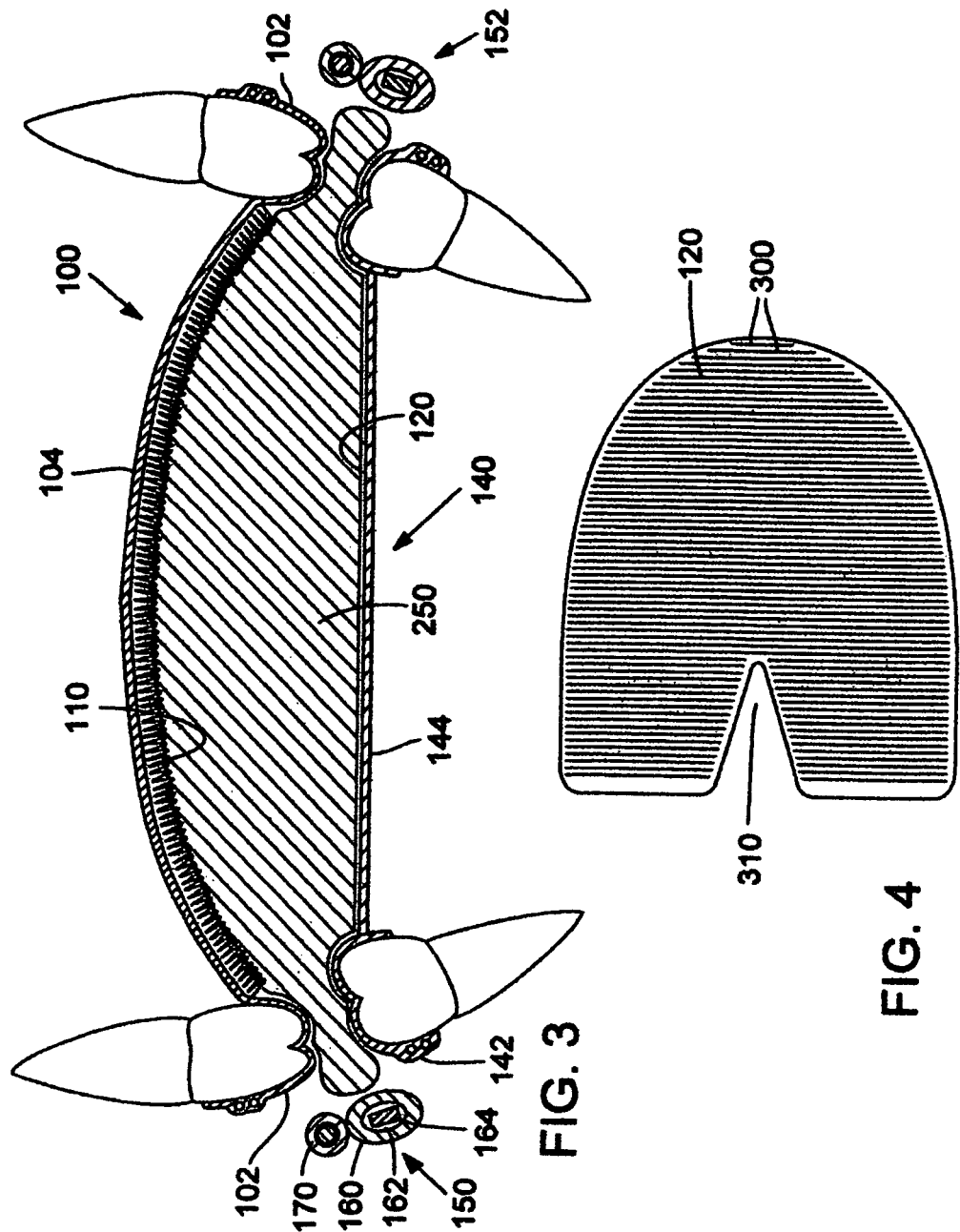

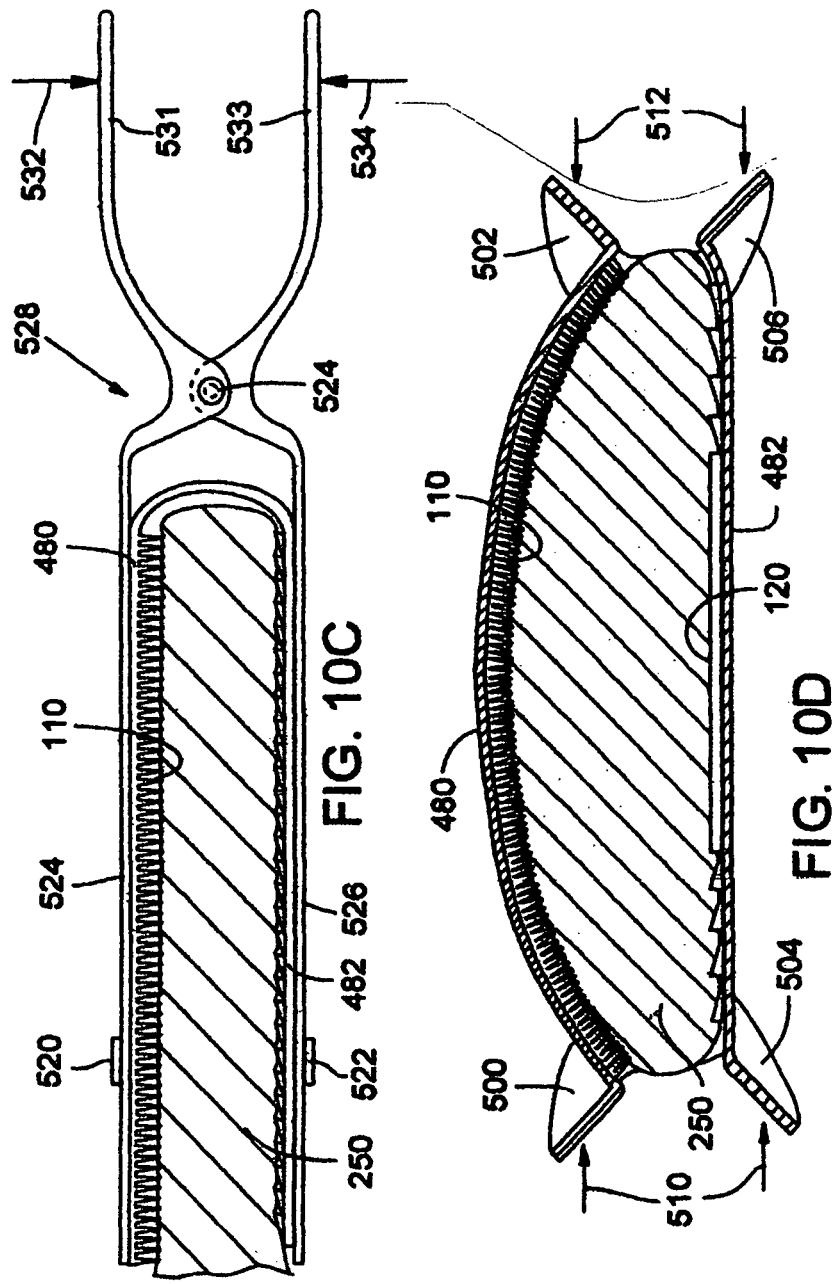

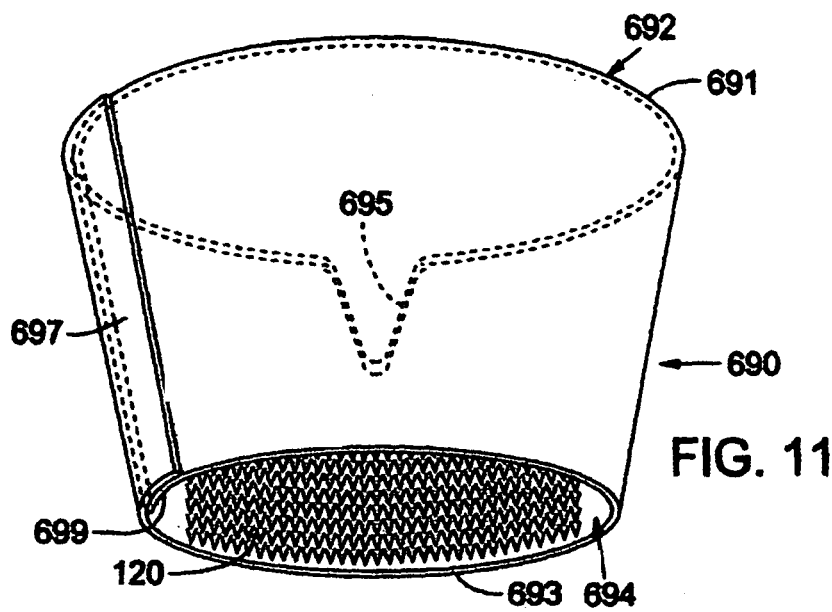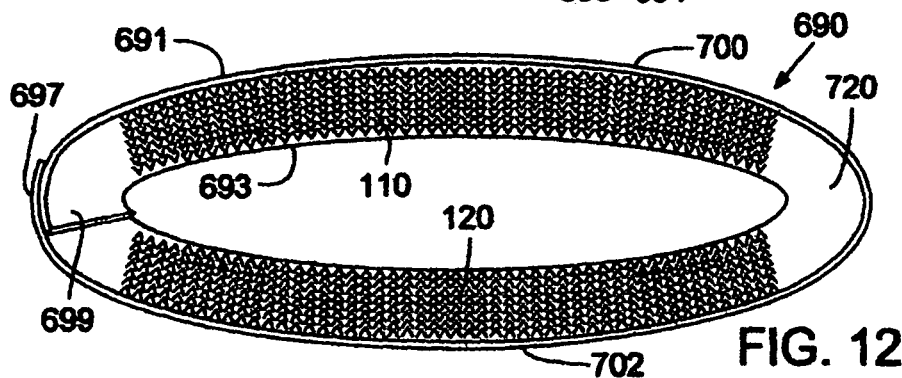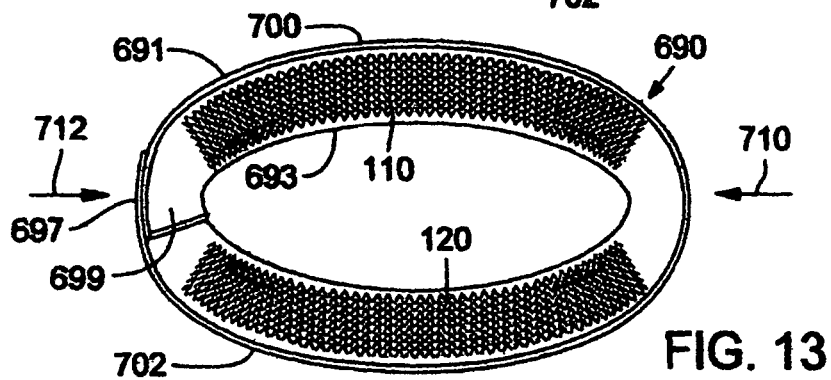

TONGUE GRASPING AND RESTRAINING APPARATUS AND METHODS

CROSS REFERENCE TO RELATED APPLICATIONS

This is the U.S. National Stage of International Application Serial No. PCT/US2006/019759, filed May 18, 2006. This application claims the benefit of U.S. Provisional Application Ser. No. 60/684,849, filed May 19, 2005, entitled "Tongue Grasping and Restraining Device for Preventing Sleep Apnea"; the benefit of U.S. Provisional Application Ser. No. 60/720,650, filed Sep. 27, 2005, entitled "Tongue Positioning and Restraining Device for Treatment of Sleep Apnea"; and the benefit of U.S. Provisional Application Ser. No. 60/758,603, filed Jan. 13, 2006, entitled "Specialized Tongue Grasping Surfaces for Tongue Restraining Device", which are each incorporated herein by reference in their entirety.

TECHNICAL FIELD

The technology disclosed herein relates to apparatus for holding an individual's tongue and to methods of manufacturing such apparatus.

BACKGROUND

The prior art describes a number of devices designed to prevent snoring and/or obstructive sleep apnea by holding the lower jawbone forward. Holding the lower jawbone forward creates some additional space in the pharynx, however, generally, obstructive sleep apnea is caused not by lack of pharyngeal space, but by the tongue dropping back and blocking the pharyngeal airway. Holding the lower jaw forward exerts some forward influence on the resting position of the tongue, since the tongue is attached to the lower jawbone. However, the tongue is only loosely attached to lower jawbone, so holding the lower jawbone forward does not necessarily hold the tongue far enough forward to prevent obstructive sleep apnea. Studies have shown that lower jawbone protrusion is a valuable tool in the treatment of obstructive sleep apnea. However, this approach alone would not be effective in many cases.

There is a need for an improved apparatus for holding an individual's tongue forward to reduce the risk of sleep apnea.

SUMMARY

In certain embodiments, an apparatus grasps an individual's tongue by squeezing it from above and below between tongue gripping surfaces. The device then restrains the tongue from retrusion by coupling to the upper jaw, such as by engaging the upper teeth. Because of the effectiveness of the tongue gripping surfaces, the device can hold the tongue securely all night without compressing the tongue sufficiently to cause pain or discomfort. For example, although variable, tongue compression forces of less than from one to two pounds, for example one-half pound or even less can be sufficient to restrain the tongue. The tongue gripping surfaces can be comprised of projections, such as a large number of densely arranged points or blades. These projections can project at an angle toward the tip of the tongue. The biasing force to squeeze the tongue gripping surfaces against the tongue can be provided by suitable biasing mechanisms, such as springs or rubber bands. The attachment to the upper jaw can be provided by mechanisms, such as an upper dental appliance or denture, a mouthpiece, an adjustable arm which terminates in a flange abutting the front surfaces of one or more upper front teeth, or a length of the material, such as dental floss fastened to one or more of the upper front teeth.

The tongue gripping surfaces in exemplary embodiments can be curved to more closely follow the contour of the tongue, especially the upper surface of the tongue.

Mechanisms can also be provided in embodiments to assist in separating the upper and lower tongue gripping surfaces to facilitate the insertion and removal of the tongue.

In accordance with some embodiments, an apparatus grasps an individual's tongue by squeezing it from above and below between tongue gripping surfaces. The apparatus of such embodiments is desirably coupled to the upper jaw, such as by a mechanism that engages the upper teeth to minimize the risk of retrusion of the tongue.

The tongue gripping surfaces can be comprised of plural projections, such as a large number of densely arranged points or blades. The projections, or selected portions thereof, can be supported at a forwardly extending angle toward the tip of the tongue. A biasing force desirably urges the tongue gripping surfaces toward one another to grip the tongue. Exemplary biasing mechanisms comprise springs, elastic bands, or the resiliency of material comprising the apparatus. Coupling to the upper jaw can be provided by suitable jaw coupling mechanisms, such as an upper dental appliance or denture, an arm, that can be adjustable, the arm terminating in a flange abutting the front surfaces of upper front teeth, an elongated tie such as a length of dental floss fastened to one or more of the upper front teeth, and/or a molded upper teeth engaging mouthpiece.

In one exemplary embodiment, the upper and lower tongue gripping surfaces are carried by upper and lower dental appliances which are biased together, such as by elastic bands. Telescoping mechanisms, such as tube and rod mechanisms, can be used to position the lower jaw in a protruded position.

In another exemplary embodiment, the upper tongue gripping surface is carried by an upper support comprising a dental appliance, mouthpiece or upper denture and the lower tongue gripping surface is supported by a lower support that is coupled to and movable relative to the upper support, such as by a hinge or other coupler. The upper and lower supports can be biased together, such by elastic bands or springs. In one form, the coupler comprises at least one, and desirably plural torsion springs. In another embodiment, the upper and lower supports are coupled together by a coupler that resiliently urges the supports and tongue gripping surfaces together.

In another embodiment, upper and lower tongue gripping surfaces comprise portions of a resilient clamp that is biased closed by the resiliency of the material, such as by a flat spring portion of material that couples the upper and lower tongue gripping surfaces together.

In yet another embodiment, upper and lower tongue gripping surfaces are incorporated into, or comprise portions of, a resilient pouch-like structure. The pouch-like structure in one form can be opened by squeezing inwardly at its sides.

Various approaches can be used in manufacturing the tongue gripping surfaces. One exemplary approach comprises forming a flexible mold by injecting a rubber molding material onto, and a few millimeters into, a surface comprised of the tips of a large number of pins set in a base, wetting the resulting mold thoroughly with acrylic monomer, and then adding powdered acrylic polymer to the mold until a base thickness of acrylic is established. Other materials can be used in this approach. Another exemplary manufacturing method comprises inserting numerous small staples into a base that, for example can be of flexible material, such as fabric. The base can be adapted to fit the contours of a user's dental appliance, and affixed to the appliance, such as by embedding the base into dental acrylic. As a further exemplary manufacturing approach, multiple small areas of a substrate or panel can be partially cut out, leaving a hinge portion coupled to the panel, these cut areas can be pushed out, such as by using a stamping process so as to protrude as multiple projections from the surface of the panel. The projections can be angled toward the tip of the tongue. Yet another approach comprises cutting, or etching, transverse grooves in a substrate or panel to create a textured surface of projecting blades. As a further approach, strips of wire mesh can be cut to leave exposed mesh tips after embedding or fastening the strips to a base. The strips are yet another form of blade or tongue engagement projections.

Desirably, exemplary embodiments are fully intraoral (totally within the mouth without protruding beyond an individual's lips) although this would not be required in less desirable embodiments.

Exemplary embodiments can restrain the tongue from retruding beyond its normal resting posture and can be worn comfortably during sleep. These embodiments desirably grasp the tissue of the tongue so effectively that little compressive force is needed to hold the tongue securely for an extended time period, such as all night. Exemplary embodiments are desirably easily openable for insertion or removal of the tongue, and desirably possess mechanisms for coupling to an individual's upper jaw, for example, via the upper teeth or an upper denture.

Various embodiments can be comprised of combinations and subcombinations of the following features and aspects.

One embodiment comprises an apparatus for grasping and restraining the tongue of a user, the apparatus comprising: a first upper support; the first upper support comprising a first tongue gripping surface, the first tongue gripping surface comprising a plurality of tongue engaging projections that extend toward the upper surface of the tongue of a user; an upper jaw coupler adapted to couple the first support to the upper jaw of the user; a second lower support; the second lower support comprising a second tongue gripping surface, the second tongue gripping surface comprising a plurality of tongue engaging projections that extend toward the lower surface of the tongue of a user; and at least one biasing member coupled to the first and second supports and adapted to urge the first and second tongue gripping surfaces together with the user's tongue positioned therebetween so as to grasp and restrain the tongue of the user.

In accordance with the one aspect, the entire apparatus, when in use by a user, can be fully positioned within the user's mouth behind the lips of the user and thereby in accordance with this aspect is entirely intraoral.

In accordance with an aspect, at least one biasing mechanism urges first and second tongue gripping surfaces together with a light compressive force, such as from about one to two pounds or less on a user's tongue positioned therebetween.

In accordance with another aspect, a first upper support can comprise a base portion with tongue engaging projections extending outwardly away from the base portion.

As a further aspect, an upper jaw coupler can comprise at least one of the following: a dental appliance, a mouthpiece, a denture, a tooth or teeth engaging projection, and an elongated tie for coupling to one or more teeth. In a specific exemplary form, the upper jaw coupler can comprise a tooth or teeth engaging projection that is coupled to the first upper support for movement relative to the first upper support to vary the distance between the tooth or teeth engaging projection and the first tongue gripping surface.

In accordance with additional aspects, the first and second tongue gripping surfaces can comprise one or more of the following types of projections or combinations thereof: multiple needle-like projections, multiple flat triangular projections, multiple blades, multiple frustoconical projections, tips of multiple staples, and the tips of severed mesh screen. As another aspect, at least a plurality of tongue engaging projections extending toward the upper surface of the tongue of a user can be of a different shape than at least a plurality of the tongue engaging projections that extend toward the lower surface of the tongue of a user. As yet another aspect, multiple tongue gripping projections that extend toward the upper surface of the user's tongue can have tips or edges sized for insertion between filliform papillae of a user's tongue.

In accordance with a more specific example, at least a major portion of the first tongue gripping surface can comprise densely arranged multiple points having a density of at least 500 points per square inch. In accordance with yet another example, the tongue engaging projections of at least the first tongue gripping surface can comprise sharp points having a length of from about 0.05 inch to about 0.1 inch and a maximum base cross-sectional dimension of from about 0.02 inch to about 0.04 inch.

As yet another more specific example, at least one of the first and second tongue gripping surfaces can comprise a plurality of spaced apart blades having a distal edge with a thickness of from about 0.01 inch to about 0.03 inch.

In accordance with another aspect, the tongue engaging projections of at least one of the first and second tongue gripping surfaces can comprise a plurality of parallel blades. As a specific example, the tongue engaging projections of at least one of the first and second tongue gripping surfaces can comprise a first set of parallel blades, a second set of parallel blades and a third set of parallel blades, the blades of the first set being non-parallel to the blades of the second and third sets, the blades of the second set being non-parallel to the blades of the first and third sets, and the blades of the third set being non-parallel to the blades of the first and second sets.

As yet another aspect, the first and second tongue gripping surfaces can each have a front portion located adjacent to or nearest to the tip of the user's tongue and a back portion located nearest to the base of the user's tongue, and wherein at least a plurality of the tongue engaging projections of at least one of the first and second tongue gripping surfaces are angled forwardly toward the tip of the tongue. As a more specific example, at least a plurality of the tongue engaging projections of said at least one of the first and second tongue gripping surfaces can be angled forwardly at an angle of from about 45 degrees to about 85 degrees.

In accordance with another aspect, at least a portion of the first tongue gripping surface can be concavely curved in a transverse direction relative to a user's mouth so as to more closely follow the contour of a the upper surface of user's tongue. In an additional aspect, at least a portion of the first tongue gripping surface can be concavely curved in a front-to-back direction to more closely follow the shape of the upper surface of a user's tongue. As a further aspect, at least a portion of the second tongue gripping surface can be curved in front-to-back direction and/or a transverse direction to more closely follow the contour of the lower surface of the user's tongue.

As yet a further aspect, the upper support can be mounted directly to or combined with the upper jaw coupler.

As another aspect, biasing members usable in the apparatus can comprise one or more of a spring, an elastic band, such as of rubber, or combinations thereof. As an example, at least one biasing member can comprise a flat spring member joining the first upper support to the second lower support at a location forwardly of the user's tongue. As another example, at least one biasing member can comprise at least one torsion spring positioned to join a forward portion of a first upper support to a forward portion of a second lower support.

As a further example of an aspect, the first upper support, the second lower support, and the flat spring can comprise portions of a monolithic sheet of material. As a further aspect, the tongue engaging projections of the first tongue gripping surface and the tongue engaging projections of the second tongue gripping surface can be formed from the same sheet of material used to form the first upper support, the second lower support and the flat spring.

As yet another aspect, the first upper support and second lower support can each comprise a respective portion of a pouch. In one form, the pouch can be annular. In one form, the pouch can be split along at least one of its sides with side-edge portions of the split side or sides of the pouch overlapping one another.

As a still further aspect, the first upper support and the second lower support can each comprise respective portions of a generally U-shaped clamp.

As yet another aspect, the second lower support can be provided with a notch that is sized and positioned to accommodate the lingual frenum of the user's tongue.

As yet another aspect, the apparatus can also comprise a second jaw coupler adapted to couple the second support to a lower jaw of the user. The second support and second jaw coupler can be comprised together, such as in a dental appliance. This form of apparatus can also comprise first and second telescoping mechanisms, such as tube and rod mechanisms positioned along respective sides of and coupled to the first upper and second lower supports. Each of the tube and rod mechanisms can comprise first and second end portions coupled at one of the first and second end portions to one of the first upper and second lower supports and coupled at the other of the first and second end portions to the other of the first upper and second lower supports. As a more specific example, in one form, each tube and rod mechanism can comprise a first sleeve portion having a rod receiving bore, a rod slideably received by the rod receiving bore, a second threaded sleeve portion mounted to the first sleeve portion and a threaded support coupler threaded into the second sleeve portion, wherein rotation of the threaded support coupler shifts the threaded support coupler into and out of the second threaded sleeve portion depending upon the direction of rotation of the threaded support coupler to thereby adjust the length of the rod and tube mechanism. As a more specific aspect of an exemplary tube and rod mechanism, the first sleeve portion can comprise at least one first anti-rotation surface within the bore and the rod can comprise at least one second anti-rotation surface, the first and second anti-rotation surfaces engaging one another to prevent rotation of the rod relative to the sleeve.

As yet another more specific aspect of an embodiment, first and second bias element engaging projections can be coupled to the first upper support and extend outwardly at opposed locations adjacent to the front of a user's mouth, the apparatus can comprise third and fourth bias element engaging projections coupled to the second lower support and extending outwardly at opposed locations adjacent to the front of the user's mouth, wherein at least one first biasing member, such as one or more elastic bands, can be coupled between the first and third bias element engaging projections and at least one second biasing member, such as one or more elastic bands can be coupled between the second and fourth bias element engaging projections.

The disclosure is directed to all novel and non-obvious features and method as disclosed herein alone and in various combinations and sub-combinations as set forth in the claims below. There is no requirement that specific or all advantages set forth herein need to be addressed in any one embodiment. The embodiment disclosed herein are exemplary and do not limit the scope of this disclosure.

DESCRIPTION OF DRAWINGS

FIG. 3 shows a transverse cross sectional frontal view of the embodiment of FIG. 1 positioned in a user's mouth.

FIG. 4 shows a top view of the lower tongue gripping surface of the embodiment of FIG. 1.

FIG. 10C shows an embodiment similar to that of FIG. 10 with one form of tool engageable opening assisting mechanism.

FIG. 10D shows exemplarily opening mechanisms that can be included in the embodiment of FIG. 10A for assisting in opening the embodiment to release the user's tongue.

FIG. 11 shows a perspective view of a still further embodiment.

FIG. 12 shows a front view of the embodiment of FIG. 11 in a tongue gripping position.

FIG. 13 shows a front view of the embodiment of FIG. 11 in a tongue releasing or open position.

DETAILED DESCRIPTION OF EXEMPLARY EMBODIMENTS

A number of exemplary embodiments of tongue grasping and restraining devices are described below. Two examples can be custom devices, which are typically made in a dental laboratory to fit the upper teeth or edentulous ridge. Two other examples can comprise relatively inexpensive devices that may be suitable for "over-the-counter" markets. The latter two devices in one form comprise examples of tongue clamps that can be independently attached or coupled to the upper teeth of a user. Generally, the upper teeth can be used as a source of anchorage for restraining the grasped tongue, because the upper teeth and jaw are fixed to the underside of the front of the skull, while the lower jaw is a single mobile bone. In users who lack upper teeth, an upper denture plate can be used as an upper jaw coupling mechanism.

In this disclosure, the terms "a", "an", and "at least one" means both the singular and the plural. Thus, if two of a particular element are present, there is also a, an, and at least one of these elements that is present. In addition, the term "coupled" means both direct connections between elements and indirect connections of elements through one or more other elements.

Also, a component is "embedded" in another component if at least a portion of the component is inserted into the other component. Also, the term "plural" encompasses two or more and the term "multiple" means many (e.g. at least one hundred).

Figure 1:
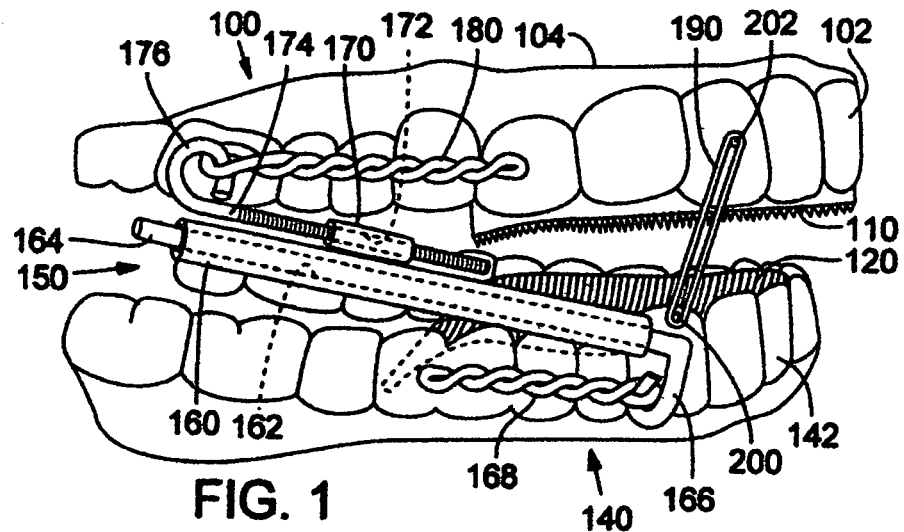
FIG. 1 shows a side elevational view of one embodiment outside of user's mouth.
Figure 2:
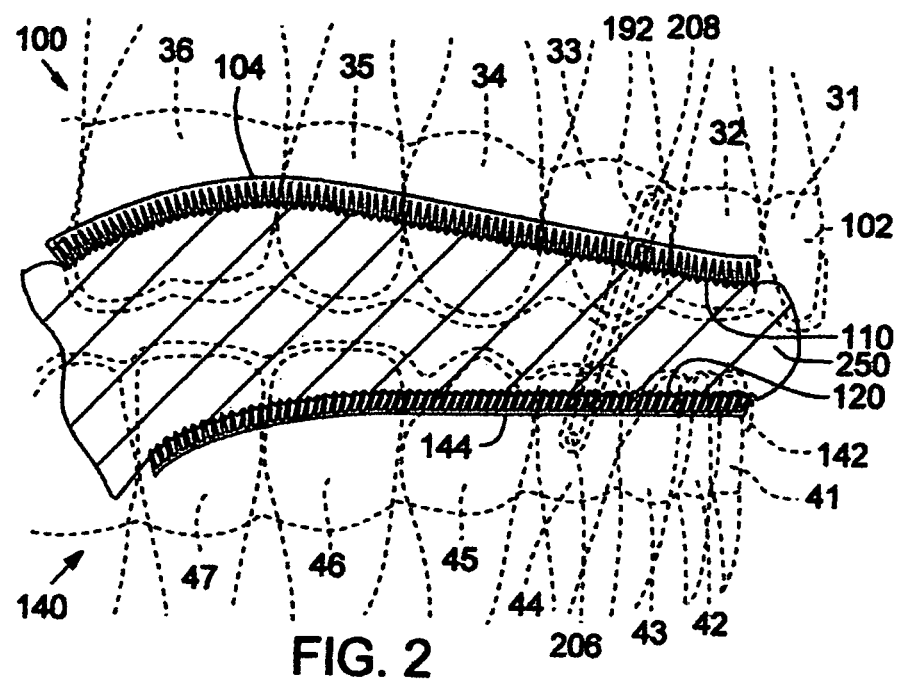
FIG. 2 shows a vertical sectional side-view through a portion of the embodiment of FIG. 1 positioned in a user's mouth.

An exemplary lower jaw protrusion embodiment shown in FIGS. 1-3 is one embodiment that typically would be made by a dentist for a person with a full or nearly full dentition.

With reference to FIGS. 1-3, an upper jaw coupler is shown in the form of a dental appliance or mouthpiece having teeth receiving portions 102 for receiving the teeth of the user. A cross-piece, plate or palate portion 104 is joined to the teeth receiving portion and comprises one form of an upper tongue gripping surface support. An upper tongue gripping surface 110 is affixed to support 104 of appliance 100. In this example, the appliance 100 is designed to cover a user's upper teeth, including teeth along the respective sides of the user's mouth. Also, in this example a lower jaw coupler 140 is shown. The coupler 140 is shown in the form of a dental appliance or mouthpiece having teeth receiving portions 142 and a cross-piece, plate or lower palate portion 144. In this example, the dental appliance 140 is designed to cover the user's lower teeth, including teeth along the respective sides of a lower jaw. In operation, the lower dental appliance 140 is held, along with the entire lower jaw bone of a user when teeth are received therein, in a protruded position, such as by telescopic mechanisms positioned along the respective sides of the apparatus. One specific example of such telescopic mechanisms comprises first and second tube and rod mechanisms (one being indicated at 150 in FIG. 1) along the sides of the teeth receiving portions of the appliances. FIG. 3 illustrates a portion of a second such tube and rod mechanism 152.

A lower tongue gripping surface 120 is affixed to the lower jaw coupler 140. One advantage of attaching the tongue gripping surfaces to a dental appliance, such as appliances 100, 140, is that appliances that cover the teeth, or at least a majority of such teeth, prevent unwanted tooth movement in response to the forces generated by holding the lower jaw bone forward. Dental appliances are usually able to distribute forces evenly the along the teeth they cover. Appliances that cover the teeth of both upper and lower dental arches prevent adverse movement of all the teeth while also being able to hold the lower jaw bone forward relative to the upper jaw by means such as telescoping tube and rod mechanisms and/or by interlocking inclines.

In the FIGS. 1-3 embodiment, the lower jaw is held in protrusion by two tube and rod telescopic mechanisms 150, 152. With reference to FIG. 1, one of such tube and rod mechanisms 150 will be described. The mechanism comprises a first sleeve 160 that is elongated and defines a longitudinally extending bore 162 therethrough. A rod 164 is slideably received within bore 162. An end portion 166 adjacent to lower appliance 140, and near the forward end of the appliance, can comprise a hook that engages a loop of an anchor 168 embedded within the appliance. A second sleeve 170 is mounted to sleeve 160, such as by welding, and can be stacked above the first sleeve. Sleeve 170 has a longitudinally extending bore 172 that is desirably threaded. A coupler 174 has an externally threaded shank portion that is threadedly received by the sleeve 170. Coupler 174 can be shaped to form a hook 176 at one end thereof. Hook 176 can engage a loop portion of an anchor 180 embedded in appliance 100. With hook 176 disconnected from the anchor, the coupler 174 can be rotated in a first direction to shift hook 176 away from sleeve 170 to telescopingly lengthen the tube and rod mechanism. In contrast, rotation of coupler 174 in the opposite direction shifts hook 176 toward sleeve 170 and shortens the length of the tube and rod mechanism. Although this construction is advantageous, other telescoping mechanisms, such as other forms of tube and rod mechanisms can also be used.

With reference to FIG. 3, the illustrated rod 164 has at least one anti-rotation surface, and in FIG. 3 the rod is rectangular in cross-section and thus has four such surfaces. In addition, the bore 162 also has at least one anti-rotation surface, for example surfaces formed by the generally oval cross-sectional shape of the interior of the bore 162. Consequently, the interior of the bore surfaces engage flat surfaces of the rod and restrict the rod 162 against rotation relative to the sleeve 160. Thus, anti-rotational cooperating surfaces are provided in this tube and rod instruction. The tube and rod mechanisms couple the upper dental appliance 100 to the lower dental appliance 140 in a manner that allows extensions/contraction of the appliances relative to one another. In this example, the anchors 168, 180 can be embedded in acrylic on the outer portions of the teeth receiving components of the appliances. When the upper and lower components of the tube and rod mechanisms are engaged in the user's mouth, the rod 164 projects through open ends of the sleeve 160 so as to permit telescopic reciprocation of the rod within the sleeve. As the user's mouth closes, the rod slides into the sleeve until the forward most open end of the sleeve abuts the hook 166 and halts the inward movement of the rod within the sleeve. This thereby halts the retrusive movement of the lower jaw bone relative to the upper jaw.

One or more biasing mechanisms can be provided for biasing upper and lower dental appliances 100, 140 toward one another. For example, elastic bands, such as rubber bands 150, 152 can engage and be stretched between biasing member coupling extensions. Thus, for example, lower lingual buttons 200, 206 can project outwardly at opposed locations from an outer surface of appliance 140 with such buttons 200, 206 being positioned toward the front of the user's mouth. Similarly, lingual buttons 202, 208 can project outwardly from appliance 100 in opposed directions with such buttons 202, 208 being located toward the front of user's mouth such as slightly forwardly of buttons 200, 206 in this example. Elastic bands 190, 192, extend between respective pairs of the lingual buttons (e.g., band 190 extends between buttons 200, 202 and band 192 extends between buttons 206, 208). Lingual buttons are commonly used in orthodontics for attaching rubber bands. Other mechanisms can alternatively be used to attach biasing members, such as rubber bands or other biasing members, to upper and lower dental appliances. Examples comprise lingual cleats, loops of wire, and structural or anchoring components that are part of a dental appliance. The attachment mechanisms can be located on the outer aspects of the appliances to allow the tongue to fit comfortably between the rubber bands or other biasing mechanisms when they are stretched taut. Plural rubber bands can be used as exemplary biasing mechanisms on each side of the appliances. Orthodontic elastic bands have been found particularly useful. As a specific example, four two ounce (light) force ⅛ inch long latex elastic bands from Dexta Corporation of Napa, Calif. have been found to apply sufficient biasing force to urge the tongue gripping surfaces 110, 120 together for holding the tongue securely without causing pain or ischemia.

In the lower jaw protrusion embodiment of FIGS. 1-3, the tongue gripping surfaces 110, 120 are separated for insertion or removal of the tongue simply by opening the user's mouth. This makes insertion and removal of the tongue easy, but does not preclude the possibility of the user's mouth opening and allowing the tongue to slip out of the space between the tongue gripping surfaces when the user is asleep.

The tongue gripping surfaces 110, 120 can be equipped with various mechanisms for frictionally engaging and grasping the user's tongue therebetween. The tongue gripping mechanisms desirably comprise a plurality of projections and most desirably include a multiplicity of such projections. The projections of tongue gripping surface 110 can be different from, identical to, or similar in part to, the projections of tongue gripping surface 120. Also, combinations of different types of projections can be used on either or both of the tongue gripping surfaces 110, 120.

Figure 3A:
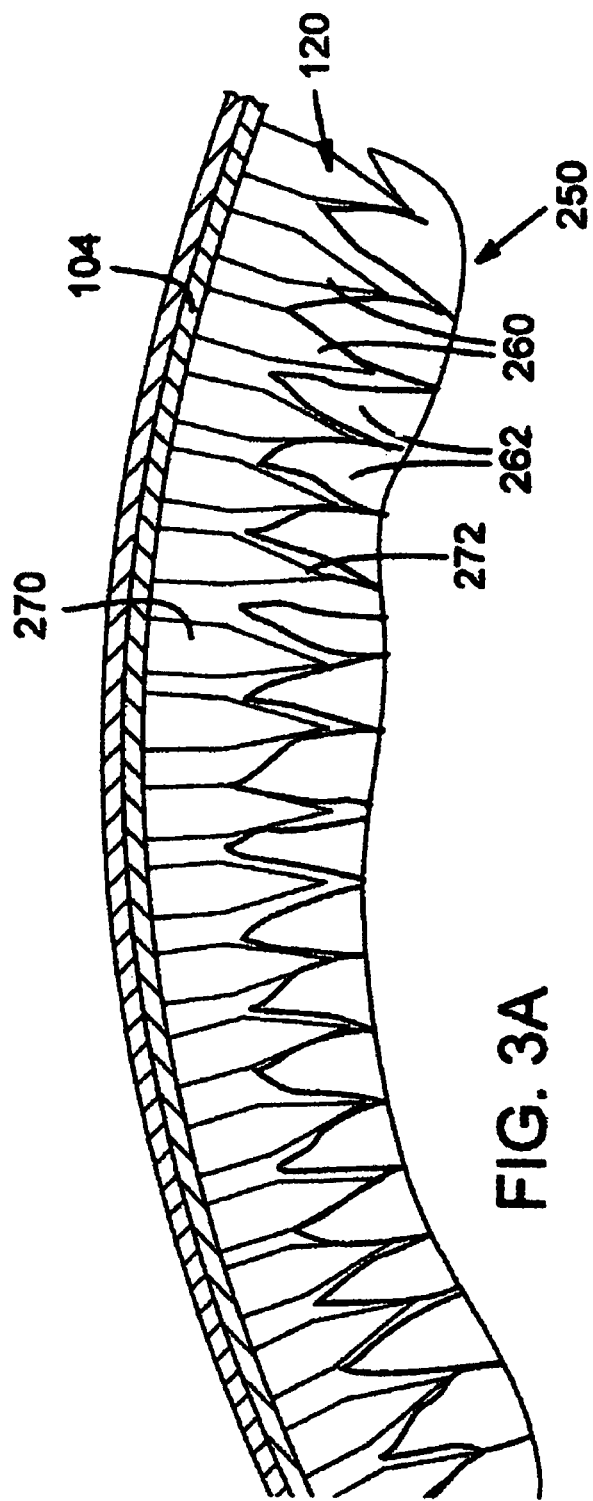
FIG. 3A shows an example of filliform papillae of a user's tongue in the process of engagement by projections of one form of an upper tongue gripping surface.

With reference again to FIGS. 1-3, the downward or tongue facing portion of upper tongue gripping surface 110 is desirably comprised of a large number of projections. These projections can be pointed projections, needle-like, or needle projections and can be configured to fit between the filliform papillae which occupy most of the upper (dorsal) surface of the front half of the tongue. These needles can be of any suitable material, such as of plastic or metal, with acrylic and stainless steel being specific examples. FIG. 2 illustrates projections of tongue gripping surface 110 bearing against the upper surface of the user's tongue 250 and projections of the gripping surface 120 bearing against the under surface of the tongue. FIG. 3A illustrates exemplary needle-like projections, some being numbered as 260, shown being positioned between filliform papillae 262 of the user's tongue as the tongue gripping surface 120 engages the upper surface of the tongue.

Figure 3B:
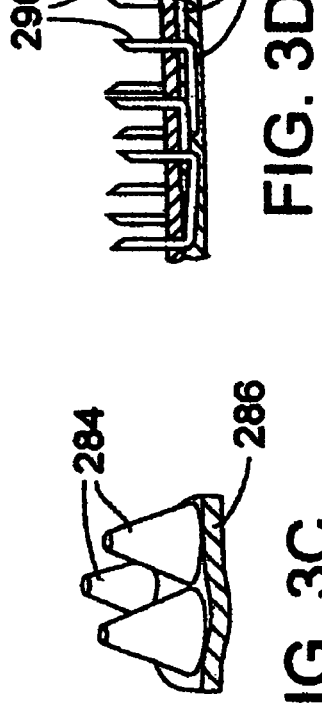
FIGS. 3B, 3C and 3D illustrate exemplary tongue gripping surfaces.
Figure 3C:
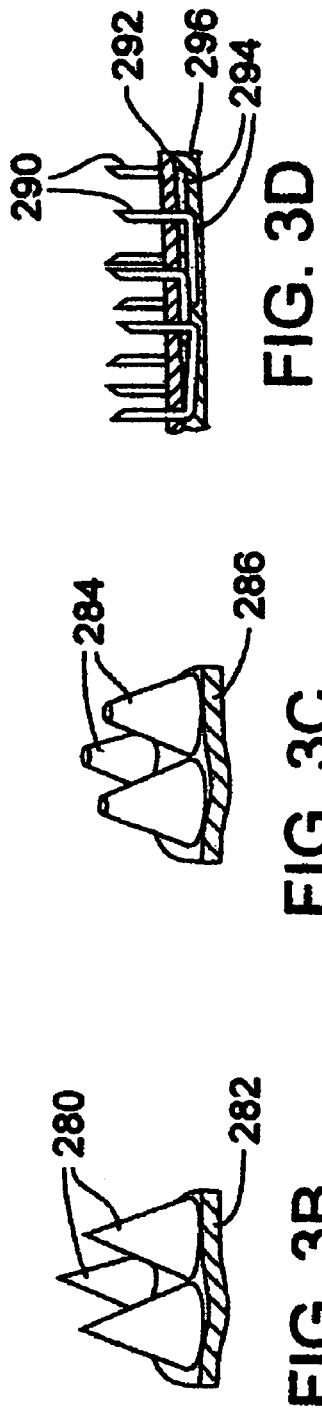
Figure 3D:
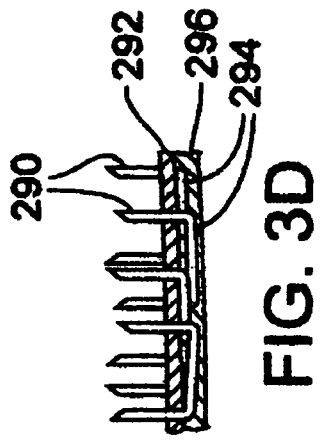

The projections can take many forms, in one specific example, like the filliform papillae, the needles can be about 0.1 inch long and about 0.03 inch in diameter at their bases. With such small diameters, two or three thousand of the needles can fit on a surface the size of upper tongue gripping surface 120. Desirably, the density of such projections is at least about 500 per inch. Although the ends of the individual needles can be very sharp, the large number of such needles provides a "bed of nails" effect that make them safe to apply to the tissue of the upper surface of the tongue without the danger of cutting the tissue. In FIG. 3A, the projections each comprise a right cylindrical base portion 270 and a tapered conical needle-like tip portion 272. In the embodiment of FIG. 3B, the projections comprise conical projections 280 projecting from a base 282. In FIG. 3C, the projections comprise frustoconical projections 284 projecting from a base 286. In FIG. 3D, the projections comprise a plurality of staples, two of which are numbered as 290 in FIG. 3D. The staples of this example extend upwardly through a flexible base 292, such as a fabric with the crowns 294 (shown for two of such staples) being embedded in material, such as acrylic 296, coating and impregnating the fabric 292. Additional acrylic can be placed above the fabric as well. The construction of FIG. 3D can be affixed to, for example, the support 104 of the appliance 100. Other examples of suitable projections are described below. Although desirable, the embodiments are not limited to the specific types or shapes of projections described herein.

FIG. 3 illustrates a cross-section, in a transverse plain through the lower jaw protrusion embodiment. As can be seen in FIG. 3, at least a portion of the tongue gripping surface 110 in this embodiment is concave so that the tongue gripping surface more closely follows the curved curvature of the upper surface of the tongue 250. In the embodiment of FIG. 3, the lower tongue gripping surface 120 is shown as being straight in transverse cross-section. However, this surface can similarly be concave at least in part to more closely fit the contour of the undersurface of the user's tongue. With reference to FIG. 2, at least a portion of the upper tongue gripping surface 110 can also be concave in a front to back direction to again closely follow the contour of the user's tongue. In addition, a portion of the lower gripping surface 120 can also be curved, for example concave, in a front to rear direction to more closely fit the lower surface of the user's tongue. It should be noted that these curvatures are not required but do assist in providing a greater surface area of the tongue gripping surfaces in contact with the tongue to thereby enhance the retention of the tongue between the tongue gripping surfaces. Thus, in this exemplary form, the projections forming the upper tongue gripping surface generally follow the same curve as the top of the tongue or the underside of the hard palate of the user. Desirably, the upper tongue gripping surface shown in FIG. 3 extends laterally to fill the area bounded by the upper teeth and rearwardly back to roughly the location of the first molar of the user's mouth. It is to be understood that the tongue gripping surface 110 can also extend laterally onto and over the biting surfaces of some of the teeth.

The projections of the upper and lower tongue gripping surfaces, or at least a plurality of such projections, can be angled forwardly to assist in tongue retention.

FIG. 4 illustrates a top view of an exemplary form of lower tongue gripping surface 120 that can be mounted to the lower dental appliance. The tongue gripping surface of FIG. 4 is comprised of numerous rows of blade-like projections, some of which are numbered at 300 in FIG. 4. In FIG. 4, the projecting blades 300 are shown parallel to one another. Desirably, although not required, the edges of the blades are angled toward the tip of the tongue as they emerge from their supporting base so that the tongue cannot easily move backward from engagement in the space between the upper and lower tongue gripping surfaces. The upper projections and lower blades can, for example, project toward the tongue tip at a desirable angle. A specific example of a projection angle is an angle of from about 45 degrees to 85 degrees, with a 75 degree angle being a more specific example. The blades can have an edge which is desirably very thin, for example 0.1 inch or less with a specific example being 0.05 inch. The edges of the blades that contact the lower surface of the tongue can also be beveled to create a sharper edge that faces the tip of the tongue.

With reference to FIG. 2, some of the user's upper teeth are shown with numbers 31, 32, 33, 34, 35 and 36. In addition, some of the user's lower teeth are shown with numbers 41, 42, 43, 44, 45, 46 and 47. With reference to FIGS. 1 and 2, it can be seen in this exemplary embodiment that there is a change in the angle of the plane or direction of the lower tongue gripping surface 120 at the location corresponding to teeth 46 and 47. To enhance the grip, the lower tongue gripping surface 120 can follow the natural curve of the underside of the tongue posteriorly down toward the base of the tongue in the user's neck. In FIG. 3, the lower tongue gripping surface 120 is depicted as flat, however it is understood that tongue gripping surface 120 can also have a concavity to fit the natural contour of the underside of the tongue.

In FIG. 4, it can be seen that a notch 310 is provided along the rearmost edge of lower tongue gripping surface 120 with a notch 310 being centrally positioned relative to the illustrated lower tongue gripping surface support. The notch 310 is shown as triangular, but it can be of other shapes. This notch is provided to accommodate the lingual frenum, a fiberous attachment between the underside of the tongue and the lower jaw bone. Alternatively, the support for the tongue gripping surface 120 can be shortened in the rearward direction to terminate forwardly of the lingual frenum with a notch then not being provided. As yet another alternative, a flexible membrane or other flexible component can be provided at such location to accommodate the lingual frenum.

Figure 5:
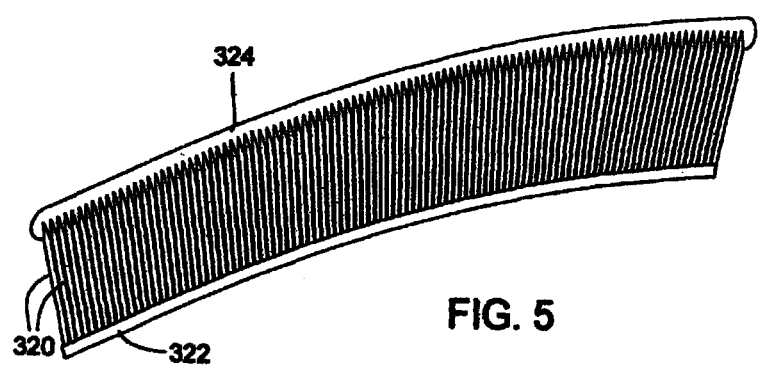
FIG. 5 shows a side view of the mold used in one exemplary manufacturing approach used to fabricate one form of upper tongue gripping surface.

Various approaches can be used to fabricate the projections of tongue gripping surfaces 110, 120. One exemplary approach for fabricating needle-like projections of the upper tongue gripping surface 110 of the embodiment of FIG. 1 will be described in connection with FIG. 5. With reference to FIG. 5, a plurality of mold forming pins, some of which are numbered as 320 in FIG. 5, are supported to project upwardly from a mold pin supporting base 322. Flexible molding material 324 is utilized in this approach to take an impression of the surface formed by the collection of pin points or tips of the pins 320. Although not shown in FIG. 5, the pins 320 can be supported parallel to one another and angled in one direction relative to the base 322 (this results in the molding of tongue engaging projection pins angled forwardly toward the tip of the tongue when the mold is used). The base 322 can be a rigid base, such as one made of plaster and wax which holds the pins so that they do not pull out of the base when the fully set molding material 324 is pulled off the collection of pin points. However, base 322 can also be a flexible base, such as a tightly woven nylon fabric, held under a collection of pins 320 which are tightly enclosed by a surrounding framework, such as by a thick rubber band, so that the pins can freely move up and down relative to each other and thereby the plane of the pin tips can be adjusted to fit any desired surface contour by simply placing flexible base supporting such pins on a surface with the appropriate contour.

In one approach to manufacturing the mold 324, a flexible molding material, such as polyvinylsiloxane, is placed or expressed onto and about 1 mm to 3 mm into the surface of the pin points of pins 320, allowed to set, and removed. A base material, such as fabric cloth, can be placed over the polyvinylsiloxane after it has been expressed onto the pin points to receive some of the molding materials and give the mold tensile strength to facilitate removal of the mold without tearing it.

The resulting mold 324 can then be used to form a tongue gripping surface. For example, the mold 324 can be used to form a tongue gripping surface of acrylic or other plastic. As a specific example, the mold can be thoroughly wetted with acrylic monomer or other plastic solvent or polymerizing agent. A brush can be used to release trapped air bubbles from the mold. A powdered polymer can then be added to the wetted mold until a sufficiently thick mix of polymerized plastic, such as acrylic, is built up within the mold. Thus, a tongue gripping surface resulting from the use of the mold comprises plural needle-like points supported on an acrylic base. Adding polymer to a mold surface that has already been thoroughly wetted with monomer allows the material, such as acrylic, to reach the full depth made by the impression of the pin points in the mold and thereby create tongue gripping points that are almost as sharp as the pins 320, which can be comprised of steel, used to make the mold. Vibration can also be used to enhance the distribution of the powdered polymer into the monomer in the ends of the pin point mold depressions. A vacuum can be used to assist in removing trapped air bubbles. The pins 320 can be of other shapes at their tips to result in a tongue gripping surface having alternative shapes.

In one approach for making a tongue gripping surface, such as lower tongue gripping surface 120 comprised of numerous parallel blades, numerous narrow parallel cuts of from about 0.005 inch to 0.01 inch deep in a panel of a thickness of 0.010 inch to 0.030 inch can be made. The sheet, for example, can be sheet metal such as 300 series stainless steel. Other metals or plastics can also be used. To increase the resistance to rearward movement of the tongue from between the tongue gripping surfaces, the ends of the blades can be beveled so that their edges are proclined toward the tip of the tongue when in use in a user's mouth. Alternatively, the blades can also be set, such as in parallel, in a resin or other base. Small serrated blades such as jewelers saw blades mounted in a base have been found to be very effective. Alternatively, plastic blades, such as of acrylic, can be fabricated by making a mold having a surface of saw blades, wetting the mold with acrylic monomer, and then filling the mold with polymer in the same manner as described above in connection with making needle-like projections on a tongue gripping surface. As yet another approach, strips of stainless steel mesh can be cut. The cut side edge of such strips will have projecting mesh wires. The opposite side edge can be embedded or secured to a base to comprise a tongue gripping surface of blades formed of such mesh strips.

Figure 8:
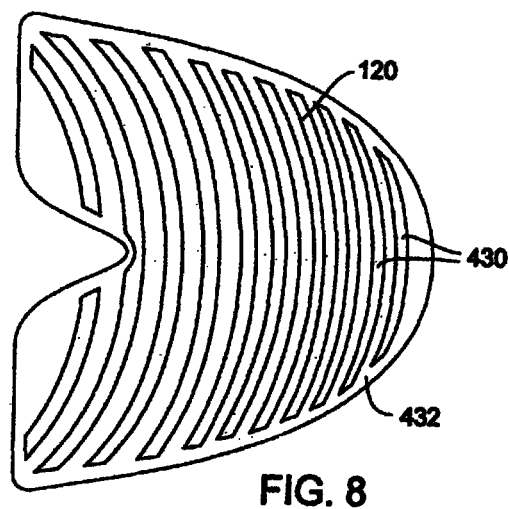
FIG. 8 shows a top view of another form of lower tongue gripping surface.
Figure 6:
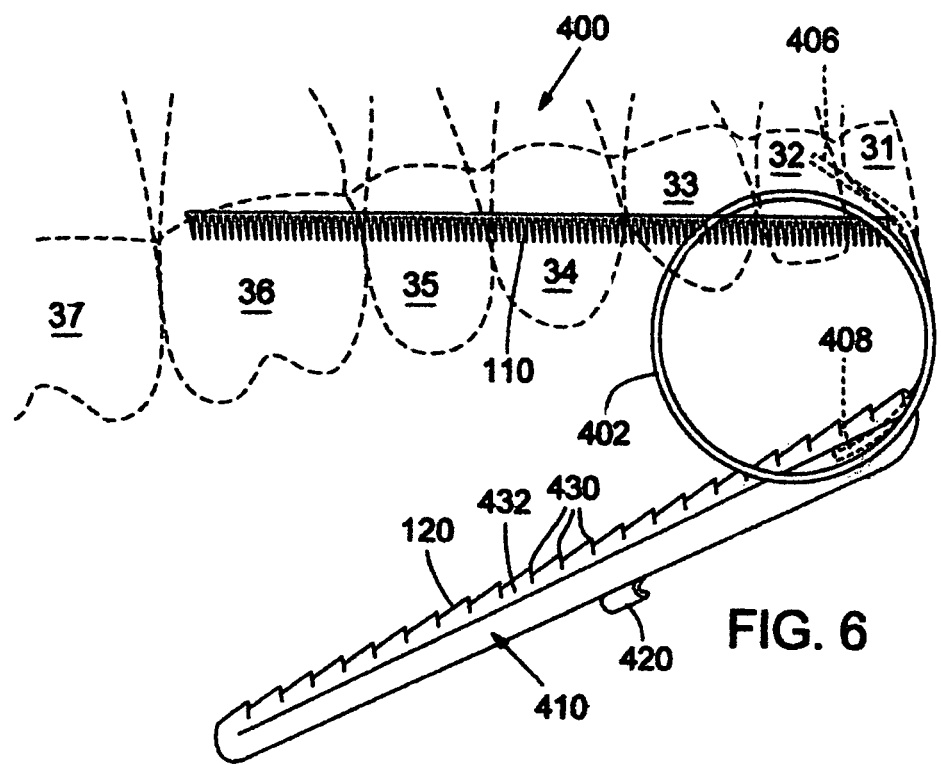
FIG. 6 shows a vertical sectional side view of another embodiment, with upper and lower tongue gripping supports in an open tongue receiving position.
Figure 7:
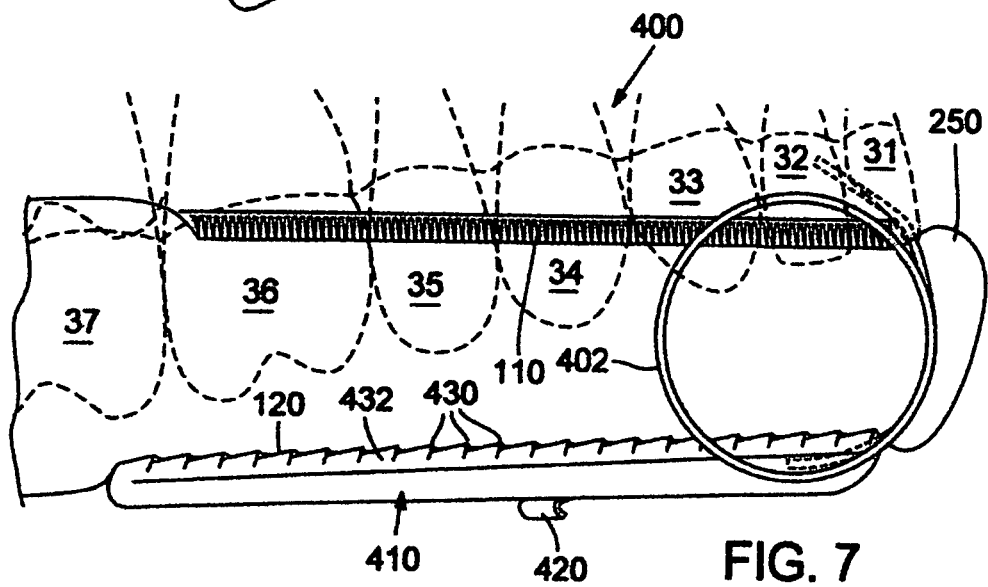
FIG. 7 shows the embodiment of FIG. 6 after it has been allowed to close to grip the user's tongue.

FIGS. 6-8 illustrate yet another embodiment of a tongue gripping and restraining apparatus. This embodiment is particularly useful for people who have no upper teeth. However, this embodiment can also be used for other individuals. For individuals without upper teeth, a suitable mechanism for attaching the tongue restraining apparatus to the upper jaw can be by means of an upper denture or base plate that maintains a good fit against the palate and edentulous ridge. The lack of upper teeth provides a great deal of clearance space for accommodating biasing mechanisms, such as torsion springs or other hardware in an upper denture or base plate. Also, a well fitting upper denture or base plate provides sufficient anchorage to the upper jaw to resist retrusion of the tongue when the apparatus is in use.

In the embodiments of FIGS. 6-8, the numbered teeth correspond to teeth of a denture. In this embodiment, the upper tongue gripping surface 120 is mounted to or coupled to a denture 400 that includes the illustrated denture teeth. A base plate, normally used to fabricate a denture, can alternatively be used. Also, for a user with teeth, a dental appliance, mouthpiece, or other jaw coupler can be used. The tongue in this embodiment is held up against the underside of the upper denture and against tongue gripping surface 120 by a biasing mechanism such as first and second spaced apart torsion springs 402 (only one of them being shown in these figures). As a specific example, the torsion springs can be five coil, 0.030 inch thick wire stainless steel torsion springs (part TO-5041 from Century Spring Corp., of Los Angeles, Calif.). Spring 402 is shown in FIG. 6, while its counterpart at the opposite side of the device is not shown. The springs can be anchored in any convenient manner to portions of the illustrated device. For example, each spring 10 can include a first leg portion 406 embedded in the upper denture 400 and a second leg portion 408 embedded in a lower support 410 that carries the lower tongue gripping surface 120. The lower tongue gripping surface support 410 can comprise, for example, a plate. The surfaces 110 and 120 can have contours as previously described.

In this FIG. 6-8 example, the lower tongue gripping surface 120 is not attached or coupled to the lower jaw of the user. Consequently, opening the jaw will not pull the lower tongue gripping surface 120 away from the upper tongue gripping surface 110. As a result, other approaches can be utilized to separate the tongue gripping surfaces so that the tongue can be inserted and removed from between such surfaces. In one specific approach, the tongue gripping surfaces can be separated for insertion or removal of the tongue by the user grasping a handle 420 on the underside of lower support 410, such as between two fingers, and simply pulling downwardly on the handle 420. Handle 420 can take any suitable form. In one specific example, the handle comprises a piece of stainless steel right-angle that is perforated at locations such that the perforations and the handle can be embedded in acrylic. The handle can be otherwise attached to or coupled to lower support 410. A wide variety of mechanical mechanisms can be used to separate the tongue gripping surfaces to facilitate insertion or removal of the tongue. Other approaches can include the user simply grasping the sides of the lower support 410 to pull lower support downwardly and away from the upper support. As another alternative, tools or other mechanisms can be used for this purpose. Thus, for example, a length of dental floss can be coupled to the lower support 410 at a location spaced rearwardly of torsion spring 402 and pulled to separate the upper and lower tongue gripping surfaces 110, 120.

FIG. 6 illustrates a side view of this embodiment in an open position ready for insertion of a user's tongue. FIG. 7 shows this embodiment after it has been allowed to close around a user's tongue 250. The tongue 250 is shown slightly compressed in the areas located directly between the upper and lower tongue gripping surfaces 110, 120. As a specific example, the compressive force applied by the torsion spring is approximately one-half of a pound. This force can be increased by using additional biasing mechanisms, such as elastic bands, attached to the upper denture 400 and to the lower support 410, much like the bands used to bias some examples of the FIG. 1 embodiment. Other biasing mechanisms can be used to provide this additional biasing force.

The upper tongue gripping surface 110 and the lower tongue gripping surface 120 of the embodiments of FIGS. 6-8 can be like those previously described in connection with the embodiments of FIG. 1-3. As another specific example, numerous parallel densely arranged 0.01 inch thick stainless steel wires projecting downwardly from a base or from the denture can be used. As a specific example, at least several hundred lengths of wire protruding downwardly into the tissue at the top of the tongue from a base affixed to the upper denture 400 can be used. Wires of up to 0.05 inch in diameter can also be used, as well as other cross sectionally dimensioned wires, but larger numbers of smaller diameter wires are more desirable. Such small wires more effectively engage the upper surface of the tongue because they fit between the filliform papillae which occupy most of the tongue upper surface.

FIG. 8 illustrates a top view of an alternative form of lower tongue gripping surface 120 that can be used in the embodiments of FIGS. 6-8 as well as in the embodiments of FIGS. 1-3. In the embodiment of FIG. 8, the lower tongue gripping surface 120 is comprised of long curving blades, some of which are assigned the number 430 in this figure. Such blades can generally follow the outer border of the sides of the tongue. The blades can, for example, be embedded in or formed as a part of a support plate 432. Dental acrylic or other resins can be used as well as other materials, to accomplish such embedding. The support plate 432 can then be mounted to the lower support 410.

The upper tongue gripping surface 110 can be made in any convenient manner, such as previously described in connection with FIGS. 1-3. As a specific example, the approach described previously in connection with FIG. 3B can be used. Thus, in accordance with this example, the upper tongue gripping surface 110 of FIG. 6 can be fabricated to fit the contour of the top of the user's tongue or the downwardly facing surface of the user's palate for an upper denture by first penetrating a flexible support, such as of fabric, with miniature staples and then embedding the fabric or support with the connecting portions (the crowns) of each staple in the acrylic of the denture. The staples can be made of stainless steel wire that is roughly, for example, 0.01 inch in diameter. The legs of the staples can be about 0.12 to 0.2 inches long and the crowns of the staples can be about 0.12 inch long. These dimensions can be varied. Although a specific example of a staple supporting base is fabric, the base can be made of any suitable material such as a poured resin. The base is fixed or mounted to the downwardly facing surface of the upper denture or support 400, such as in a dental laboratory by embedding the base and crowns of the staples in dental acrylic.

The lower tongue gripping surface can be prefabricated in stock sizes by bending a length of narrow (for example 0.02 inch wide) stainless steel shim stock, that is, for example, 0.004 inch thick, into curves. These curves for example can form a flat or gradually curved plane of generally parallel blades. One side of the edge of the blades can be secured to, such as embedded into, a base, for example of plastic. A single length of shim stock is shown in the illustration of FIG. 8. It is understood that a smaller number of somewhat shorter lengths can be used for convenience. The blades can be mounted or coupled to a base, for example set into a thermoplastic base, or a resin base can be poured around the blades. The shim stock can be serrated like a saw blade or given other contours to better grip the lower surface of the tongue. Other mechanisms for manufacturing blade-like tongue restraining structures and embedding them in a support can also be used.

Desirably, the use of upper and lower tongue gripping surfaces provides a frictional engagement of the tongue. No vacuum is required to hold the tongue in place using these devices.

Figure 9:
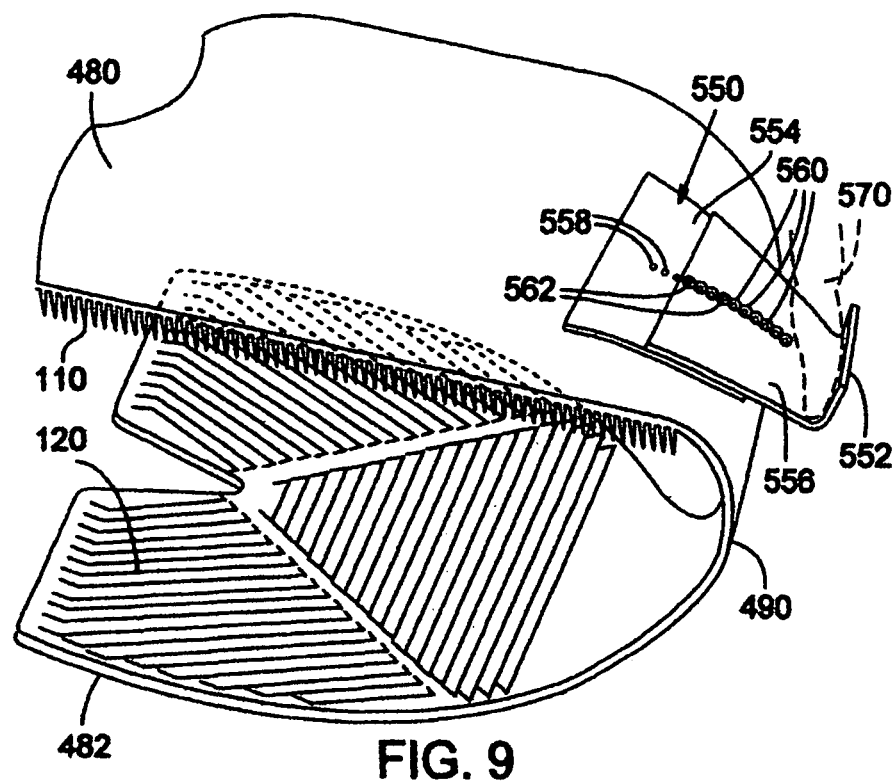
FIG. 9 shows a perspective view of yet another embodiment.

FIG. 9 illustrates another embodiment of a tongue gripping and restraining apparatus. This embodiment in one form comprises a flat spring embodiment that can be prefabricated in a relatively inexpensive version that can be provided in stock sizes, such as for over-the-counter distribution. However, such devices can also be distributed by dental professionals, or by others who have been trained to do so.

Figure 10:
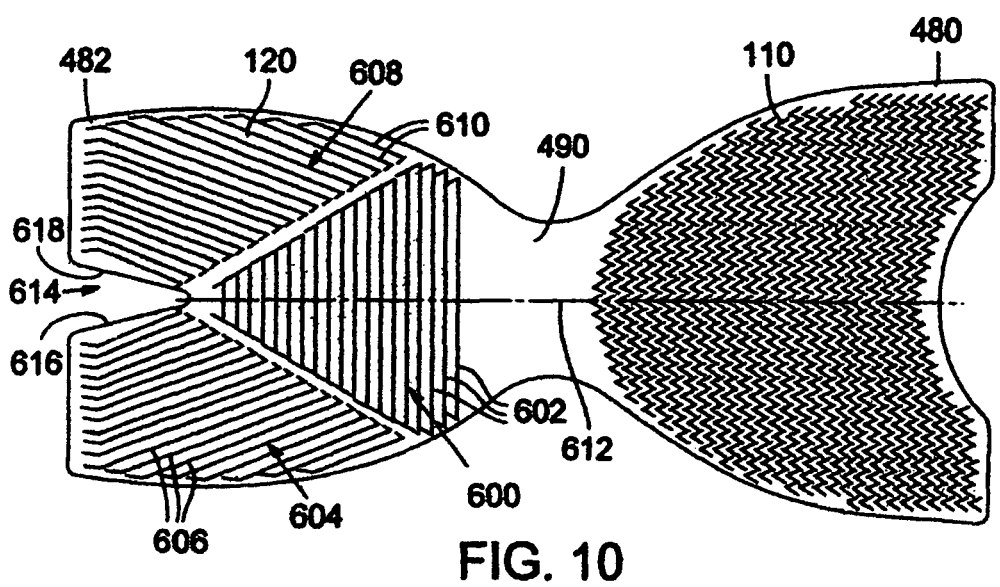
FIG. 10 shows a top view of an exemplary substrate, such as a panel, that can be used in manufacturing the embodiment of FIG. 10.

In the embodiments of FIGS. 9-10D, an upper support portion 480 is shown from which tongue gripping surface 110 projects or is carried. Also, a lower support 482 is shown from which upwardly projecting tongue gripping surface 120 projects or is carried. The support 480 can be secured to, coupled to, or embedded in a dental appliance, denture, mouthpiece, or other jaw coupler. In the illustrated example, this has not been done. Instead, supports 480, 482 are joined together at a forward end portion of the apparatus by a portion 490 so that elements 480, 482 are in effect a clamp. That is, the spacing of the tongue gripping surfaces 110, 120 is less than the thickness of the user's tongue (and can be adjusted by simply bending the member 490 in this example more or less. Member 490 desirably comprises resilient material and thus acts as a flat spring to maintain compressive forces that urge the surfaces 110 and 120 together when a tongue is positioned therebetween. The tongue gripping surfaces 110, 120 are simply spread apart to permit insertion of the user's tongue. The clamp-like structure, which can be generally U-shaped in longitudinal section, is thus of a relatively simple construction. The clamp can be opened against the bias of the flat front spring portion 490 to permit insertion of the tongue and then allowed to close against the tongue.

The components 480, 482 and 490 can be formed of a single monolithic piece of material, such as from sheet material. In addition, the projections of the tongue gripping surfaces 110, 120 can also be formed from the same sheet of material. As a specific example, stainless steel sheet material can be used. The bias can be provided by spring portion 490. If portion 490 is not a spring, the bias can be provided or enhanced by another biasing mechanism, such as attached to the supports 480, 482 to urge such supports toward one another. For example, elastic bands attached to the upper and lower tongue gripping supports can be used for this purpose, or elastic bands entirely surrounding the upper and lower supports 480, 482 can be used. The tongue gripping surfaces 110, 120 can be provided with curved contours to better fit the general curve of the gripped tongue surfaces. For example, in FIG. 9, the upper tongue gripping surface 110 has at least a portion thereof that is curved in a transverse (side to side) direction to better fit the general curve of the upper surface of the tongue.

Portions 480, 482 can include handles or points of selective attachment or engagement by a user's fingers or by tool to assist in spreading the tongue gripping surfaces to facilitate insertion of a tongue into and removal of the tongue from the space between the tongue gripping surfaces. As described in greater detail below, sheet stock can be used in one approach for manufacturing devices such as that shown in FIG. 9. With references to FIG. 10A, a plurality of finger engaging tab portions 500, 502 and 504, 506 are provided. Tab portions 500 and 502 in this example are included in the support portion 480. In addition, tab portions 504 and 506 in this example are included in support portion 402. These tab portions can be bent along fold lines in a direction away from the respective tongue gripping surfaces 110, 120. This can be best seen with reference to FIG. 10D. By exerting inwardly directed forces in the direction of arrows 510 and 512 against the tab portions, for example by using the fingers of the user of the device, the gripping surfaces 110, 120 are spread apart to facilitate insertion and removal of the tongue. With the tongue in place between the tongue gripping surfaces, removal of side forces applied in the direction of arrows 510 and 512 allows the tongue gripping surfaces 110, 120 to again close and grip the tongue therebetween.

With reference to FIG. 10C, an upper slot defining tool engaging projection 520 is centrally positioned along the upper surface of support 480 and is coupled to this support. In addition, a second slot defining tool engaging projection 522 is coupled to the lower surface of support portion 482. A leg 524 of a tong-like tool 528 can be inserted into the slot defined by projection 520. In addition, a leg 526 of the tool 528 can be inserted into the slot defined by projection 522. In this example, the legs 524, 526 are pivoted together at a location 530 and have respective handle portions 531, 533 extending beyond the pivot. Applying forces in the direction of arrows 532, 534 to the respective handles 531, 533 causes the legs 524, 526 to move apart and spread the tongue gripping surfaces 110, 120 away from one another. Thus, the squeezing of extraoral handles 531, 533 together produces an intraoral separation force between the upper and lower tongue gripping surfaces.

In use, the tongue gripping surfaces 110, 120 of the FIGS. 9, 10C and 10D embodiments can be open by pulling apart the upper and lower tongue gripping surfaces. The user's tongue can then be placed into the space between the tongue gripping surfaces. The tongue can be positioned all the way into a curved transition section 490 of the apparatus. With the tip of the tongue (a particularly tender area) pushed all of the way against the curved area 490, the tongue tip is protected from compressive forces experienced between upper and lower tongue gripping surfaces 110, 120.

In the embodiment of FIG. 9, various jaw couplers can be used to couple the embodiment to the upper jaw. These couplers can be adjustable to allow forward and rearward shifting of the tongue gripping surfaces in the user's mouth. In one specific example, a projecting arm 550 extends forwardly and is provided with an upwardly projecting tooth or teeth engaging element, such as a flange 552. The flange 552 is positioned forwardly of one or more front teeth (and desirably entirely intraorally behind the lips of the user) to couple the FIG. 9 apparatus to the upper jaw of the user. The projection 550 in one specific form is adjustable to vary the space between the tongue gripping surface 110 and the front of the user's mouth. For example, projection 550 can comprise a first arm portion 554 and a second arm portion 556. A plurality of apertures, two of which are indicated at 558 in FIG. 9 are provided in arm section 554. Apertures 558 can be internally threaded. In addition, a plurality of apertures, two of which are indicated at 560, are provided through arm portion 556. The arm portion 556 can be moved forwardly or rearwardly relative to arm portion 554 and positioned to align respective apertures 560 and 558. Fasteners, such as one or more set screws 562, can be used to join arm portion 556 to arm portion 554 to fix the tooth engaging projection 552 at a desired location relative to the tongue gripping surface 110. The flange 552 desirably projects perpendicularly upwardly from arm portion 556 so as to closely fit the forward facing surface of one or more teeth, such as the tooth 570 shown in dashed lines in FIG. 9. This partial coupling or attachment to one or more front teeth prevents retrusive movement of the apparatus relative to the upper front teeth while the projection is engaged. The arm 554 can be coupled to the support 480 in any convenient manner, such as by welding or soldering.

Again, the embodiment of FIG. 9 can be coupled to the upper jaw of a user by various mechanisms, such as by embedding or securing upper portion 480 to a dental appliance or mouthpiece (such as a rubber boil and bite-type of appliance commonly used for stock athletic mouth guards), in a resin which is directly molded to fit the mouth (such as Tak thermoplastic, or in an upper denture or an upper dental appliance. In addition, other mechanisms can be utilized to couple the apparatus to the upper jaw of the user. For example, an elongated tie, such as dental floss, can be secured (e.g., through openings provided in support 480 to one or more teeth of the user to prevent retrusion of the apparatus).

In the embodiments of FIG. 9-10D, the tongue gripping surfaces can be as previously described. As another example, the upper tongue gripping surface 110 can be comprised of numerous small points projecting from a single substrate or panel, such as support 480. The points can be angled forwardly relative to the tip of the tongue, such as previously described. In one specific approach, the points comprise apices of small triangular elements of the panel which have been bent or pushed out of the plane of the panel, leaving only the bases or hinge points of the elements joined to the panel. The points can be small enough to fit fully down between the filliform papillae of the upper surface of the tongue. The tongue gripping surface 110 can be shaped in a curve which approximates the shape of the top (dorsal) surface of the tongue or the under surface of the palate.

Figure 10A:
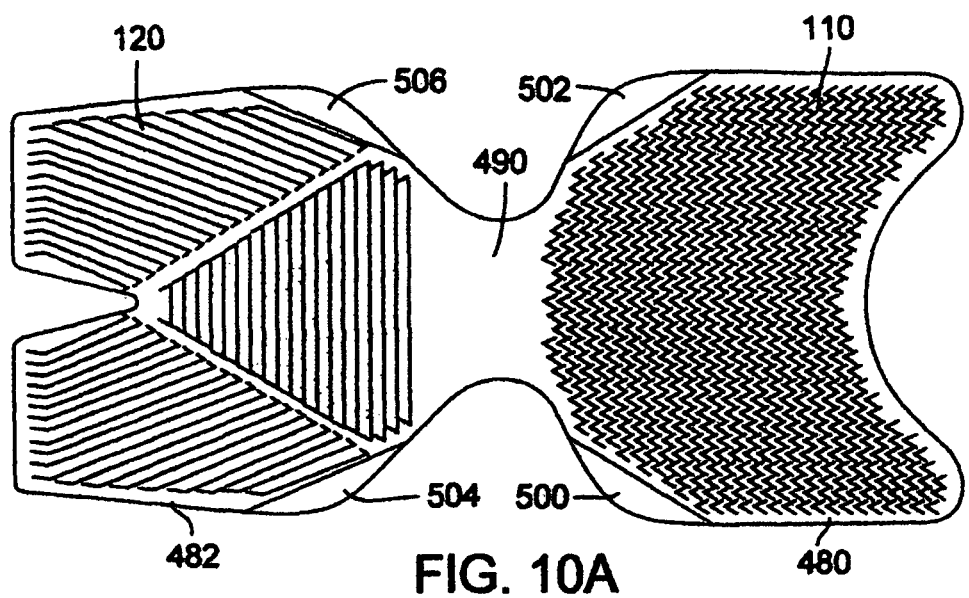
FIG. 10A shows a top view of an alternative form of substrate usable in manufacturing another embodiment.
Figure 10B:
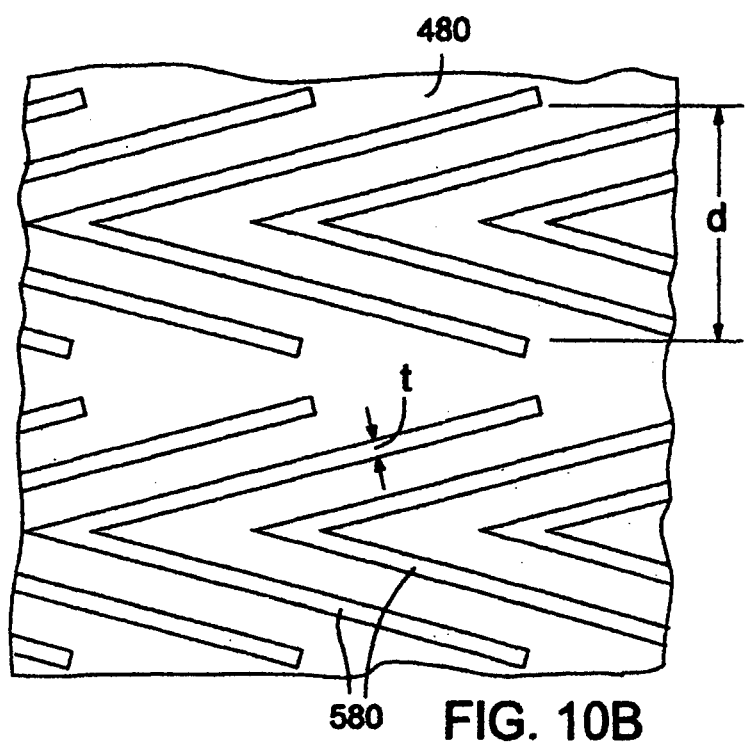
FIG. 10B shows an enlarged view of a portion of the upper tongue gripping substrate portion of the FIG. 10B embodiment.

With reference to FIG. 10B, a plurality of V-shaped slits, some of which are numbered 580 in FIG. 10B, have formed in the substrate or panel 480, these slits can be formed, for example, by laser cutting or by chemical etching. Although the slits can be varied in shape, V-shaped slits are shown in this example. The illustrated slits have a thickness T of about 0.006 inch with a base between the lower portion of each slit being of a distance d that, for example, can be about 0.025 inch. These dimensions can be varied. Following the formation of the slits, stamping or other processes can be used to bend the resulting tongue gripping projections away from substrate 480 and toward the upper surface of the user's tongue when the apparatus is in use.

As can best be seen in FIGS. 9, 10 and 10A, the lower tongue gripping surface 120 can be comprised of a plurality of blade-like structures projecting from the surface of substrate or support 482. With reference to FIG. 10, the illustrated lower tongue gripping surface 120 comprises a first set 600 of plural parallel spaced apart blades 602. In addition, this tongue gripping surface comprises a second set 604 of parallel spaced apart blades, some of which are indicated by the number 606. Also, the illustrated tongue gripping surface 120 comprises a third set 608 of parallel spaced apart blades, some of which are indicated by the number 610. In the construction of FIG. 10, the blades of set 600 are perpendicular to a longitudinal axis 612 of the apparatus. In addition, the blades of set 604 and of set 608 are skewed relative to the longitudinal axis. In addition, in this illustrated example, the blades 600 of the first set are not parallel to the blades of either the second or third sets 604, 608. In addition, the blades of the second set 604 are not parallel to the blades of the first and third sets 600, 608. In addition, the blades of the third set 608 are not parallel to the blades of either the first or second sets 600, 604. The blades of the various sets can also be angled forwardly. The blades in the front set 600 of this example are transversely oriented relative to longitudinal axis 612. In contrast, the blades of the second set of 604 are angled relative to the longitudinal axis and generally parallel an edge 616 of a lingual frenum accommodating notch 614. Also, the blades of set 608 in this example are skewed relative to the longitudinal axis 612 and are oriented generally parallel to an edge 618 of the lingual frenum accommodating notch 614. Other projection and blade orientations can be used.

This configuration of projections of lower tongue gripping surface 120 assist in minimizing excessive sideways movement of the tongue as well as retrusive movement and thus may be particularly desirable in some exemplary situations, such as for use by users who sleep primarily on their sides. Because of the ease of altering the configuration of blades in this exemplary embodiment, the blades can be arranged in custom configurations for certain situations, such as for users who only sleep on one side. Again, various combinations of different types of projections can be used for the tongue gripping surfaces 110, 120.

The embodiments of FIG. 9-10D are relatively inexpensive to fabricate. For example, such embodiments can be made from a single monolithic panel of sheet metal, such as 300 series stainless steel approximately 0.006 inch thick. Although variable, the elongated panel illustrated in FIGS. 10 and 10A has opposed parallel planner surfaces and has an overall length dimension of about 3 inches long and width dimension of about 1 inch. These exemplary embodiments are divided into respective end portions separated by a relatively narrow central portion 490. The notch 614, if provided, is desirably sized, positioned and configured to fit or accommodate the lingual frenum. The panels of FIGS. 10A and 10B can be perforated or slit along numerous V-shaped cuts in the area to form upper tongue gripping surface 110. In addition, the panel can be perforated along numerous perpendicular cuts in the area that will become the lower tongue gripping surface 120. In this example, the illustrated cuts in the upper tongue gripping surface forming area outline multiple triangles on two of their three sides. Also, the cuts that form the projections of the illustrated lower tongue gripping surface outline multiple rectangles on three of their four sides. The perforations or cuts can be made, for example, by a YAG laser or by photo chemical etching.

After the desired cuts have been made in the elongated panel, the partially cut small areas can be forced out beyond the plane of the rest of the panel. This can be accomplished by means of a stamping or other process, which leaves small elements hinged at and projecting from base portions where they attach to the panel. These projections can be angled, for example, toward the narrowed midsection 490 of the apparatus. In the upper tongue gripping surface 110, the apices of the triangles that form projections can face toward the tip of the tongue when the apparatus is in use. The angle at which the pointed projections project from the panel can be varied, with a range of from about 45 degrees to about 85 degrees being one example, and with a specific example being 75 degrees. In addition, instead of triangles and rectangles, many other shapes of areas, such as truncated triangles, squares and other shapes can be partially cut out and then bent out from the plane of the panel to create tongue engaging projections. An elongated apparatus forming sheet is desirably bent at its midsection 490 until the portions 480 and 482 are roughly in parallel planes directly opposite to each other. For example, they may be separated by a gap of about ⅜ inch and joined together by the section 490. At the same time, the support 480 can be bent into a curve that more closely fits the shape of the upper surface of a user's tongue or the underside of a palate.

FIGS. 11-14 illustrate yet another embodiment of a tongue grasping and restraining device. This embodiment is shown assembled in FIGS. 11-13 into a pouch-like or pouch structure. This embodiment can also be manufactured relatively inexpensively and can be distributed in any suitable manner, such as using over-the-counter distribution. In addition, exemplary embodiments in accordance with these figures can be manufactured from a single panel. Less desirable, they can be assembled form plural compounds.

In the embodiment of FIGS. 11-13, a pouch 690 is provided. The illustrated body is generally annular with a front edge portion 693, that is positioned toward the front of the user's mouth when the apparatus is in use and a rear edge portion 691, that is positioned adjacent to the rear of a user's mouth when the apparatus is in use. The rear edge portion can have a lingual frenum accommodating notch 695, such as previously described. When assembled, the body has a tongue receiving opening 692 and an opposed opening 694 through which the tip of the tongue can protrude. Also, the body can be split from front to rear along one side edge portion with side edges 697 and 699 positioned in an overlapping relationship. As can be seen in FIG. 12, in one specific form, the body can be generally oval in cross-section. Also, the body desirably narrows from rear to front, although this is not required. An upper tongue gripping surface 110 is supported by or formed as a part of an upper support portion 700 of the body. A lower tongue gripping surface 120 is supported by or formed as a part of a lower support portion 702 of the body.

As can be seen in FIG. 12, when assembled the exemplary apparatus is somewhat flattened. The spacing between the upper and lower tongue gripping surfaces 110, 120 is slightly less than the thickness of the tongue of a would be user. Desirably the body 690 is comprised of a resilient material, such as stainless steel, as in one example of FIG. 9. Thus, the resiliency of the body provides compressive forces against the tongue. To open the apparatus to permit insertion and removal of the tongue, inwardly directed side forces, such as applied in the direction of arrows 710, 712 in FIG. 13. These applied forces cause the tongue gripping surfaces 110 and 120 to separate so as to permit insertion and/or removal of the tongue. Removal of the inwardly directed side forces 710, 712 allows the apparatus to return to the configuration shown in FIG. 12. Rather than utilizing the resiliency of the material to accomplish compression, other biasing mechanisms can be used. For example, one or more elastic bands can surround the body to urge tongue gripping surfaces 110 and 120 together.

Upper jaw coupling mechanisms can be used in the embodiment of FIGS. 11-14, such as previously described in connection with the embodiments of FIGS. 9-10D. Thus, for example, an arm structure such as structure 550 and flange 552 (FIG. 9) can be utilized in the embodiment of FIGS. 11-13 to engage the upper teeth of the user. Alternatively, portions of the body (for example upper support portion 700) can be embedded otherwise secured to a mouthpiece, dental appliance, denture or otherwise coupled to the upper jaw of the user. As another alternative, an elongated tie, such as a length of dental floss or line can be coupled between one or more of the user's upper teeth and holes or other attachment projections provided through or coupled to the body 690.

Figure 14:
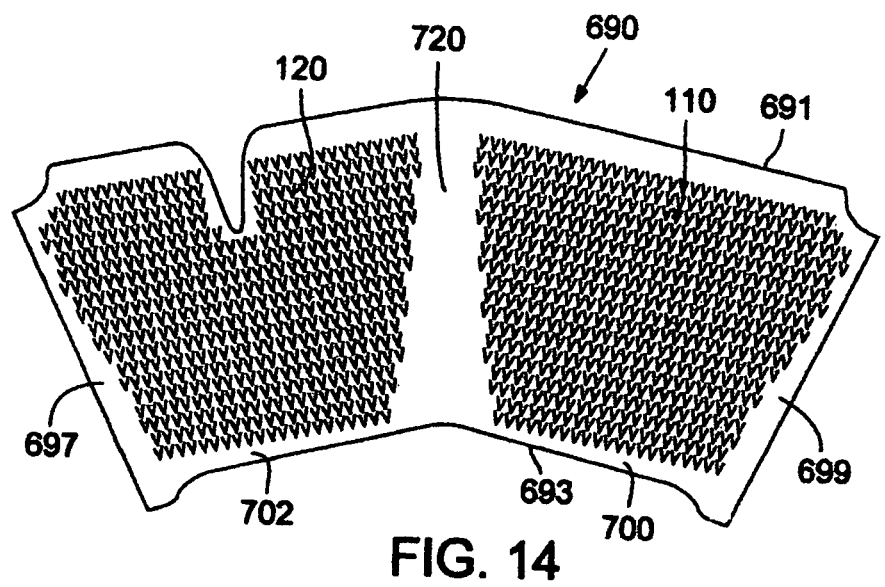
FIG. 14 shows a top view of an exemplary substrate that can be used to manufacture the embodiment of FIG. 11.

Although other approaches can be used, a single sheet, an example being shown in FIG. 14 can be used to form a structure like that shown in FIGS. 11-13. The tongue gripping surfaces 110, 120 in FIG. 14 are shown as being identical and comprise triangular shaped projections that can be formed in the manner described above in connection with FIGS. 10 and 10A. Again, other combinations of projections can be used for these tongue gripping surfaces 110, 120. The shape of the pouch-like body 690 can be generally oval in cross-section with a smaller dimension oval at the opening 694 closer to the front of the mouth than at the rear 692. As a result, the apparatus tends to fit the natural taper of the tongue toward the tip of the tongue. However, a wide variety of shapes can also be used due to the malleable nature of the shape of the tongue.

The projections formed in the sheet FIG. 14 can be formed in the same manner as the projections formed in the sheets 10 and 10A, and can comprise tongue gripping surfaces comprised of multiple points. Such points can be sized or configured to fit between the filliform papillae on the upper surface of the tongue and also can operate to grip the mucus membrane on the under surface of the tongue very effectively. A multiplicity of such points provides a "bed-of-nails" coupling effect.

As in the embodiment described above in connection with FIGS. 9-10B, a flat sheet, such as of stainless steel, can be processed by partially severing small area and then forcing them out of the plane of the sheet to form the tongue gripping projections. These tongue gripping projections can project at an angle that are positioned to face partially toward the front of the tongue to assist in gripping the tongue.

FIG. 14 illustrates a top view of one exemplary panel after the cuts have been made and before the panel has been bent into a pouch-like shape. The area 720 of the panel connecting the perforated tongue gripping surface forming areas 110, 120 can be bent so as to position areas 110, 120 at locations above and below the user's tongue. The partially cut areas of the tongue gripping surfaces can be stamped or otherwise processed to project outwardly toward the opposite tongue gripping surface and can be angled forwardly, such as previously described, toward the tip of the tongue. The sheet sections 697 and 699 are also typically bent to provide a gradual curve where such areas overlap. The bends in area 720 and in areas 697 and 699 can be generally parallel to one another and extend from the back edge 691 of the panel toward the front edge of 693 of the panel. The overlapping side sections 697 and 699 can be secured together, such as by spot welding or soldering. The area of overlap of sections 697, 699 can be in the shape of a generally C-shaped curve, that can be the mirror image of the curve of the area 720. Alternative approaches can also be use to provide upper and lower tongue gripping surfaces, such as coupling separately produced tongue gripping surface containing supports to the pouch-like body structure. In addition, the pouch can be constructed of a material of sufficient resiliency to hold the tongue between the upper and lower tongue gripping surfaces while allowing opening of the structure by pushing in on the sides of the structure.

In the above description, various types of biasing mechanisms can be used, in addition to or in combination with torsion and flat springs, the resiliency of material, and elastic bands to provide biasing forces to urge upper and lower tongue gripping surfaces together. In some cases, the only biasing mechanism necessary to hold the tongue against retrusion can be the passive stretch of jaw closing muscles, especially when large portions of the tongue are held by the apparatus between the teeth so that the teeth are forced apart significantly (at least ¼ of an inch). In addition, alternative manufacturing techniques can be used to provide tongue gripping surfaces. For example, in addition to approaches previously described, small spike-like tongue gripping projections can be made by hot stamping of a plastic panel or by using miniature round punches in a metal plate. In addition, for people with pierced tongues, the source of biasing between upper and lower tongue gripping surfaces can be a bolt or other mechanical fastener which engages upper and lower tongue gripping surfaces and extends through the pierced portion of the tongue.

Having illustrated and described the principles of my invention with reference to a number of embodiments, it should be apparent to those of ordinary skill in the art that these embodiments may be modified in arrangement in detail without departing from such principles. I claim all such embodiments and modifications that fall within a scope of any one or more of the following claims.

The invention claimed is:

1. An intraoral tongue grasping and restraining device for retaining a user's tongue in a forward position when worn by the user, the user's tongue having a tongue upper surface, a tongue lower surface, a tongue tip, a tongue base, the user having a mouth, an upper jaw and a lower jaw, said device comprising:
a first upper support comprising a first base portion and a first tongue gripping surface, and wherein said first tongue gripping surface comprises a plurality of tongue engaging projections extending outwardly from the first base portion and adapted to extend toward the tongue upper surface when worn by a user,
a second lower support comprising a second base portion and a second tongue gripping surface, and wherein said second tongue gripping surface comprises a plurality of tongue engaging projections that extend outwardly from said second base portion and adapted to extend toward the tongue lower surface when worn by a user,
an upper jaw coupler adapted to couple said first upper support to the upper jaw,
at least one biasing member adapted to urge at least one of the first and second tongue gripping surfaces toward the other of the first and second tongue gripping surfaces with the user's tongue positioned therebetween so as to grip and restrain the user's tongue,
wherein the first and second tongue gripping surfaces each have a front edge for location nearest to the tongue tip and a back edge for location nearest to the tongue base, and wherein at least a plurality of the tongue engaging projections of at least one of the first and second tongue gripping surfaces project outwardly at an angle forwardly toward the tongue tip so as to resist backward sliding of the user's tongue from between upper and lower tongue gripping surfaces.

2. The intraoral tongue grasping and restraining device of claim 1 wherein said at least one biasing member comprises at least one biasing member coupled to the first upper support and coupled to the second lower support and adapted to urge the first and second tongue gripping surfaces together with the user's tongue positioned therebetween so as to grasp and restrain the user's tongue.

3. The intraoral tongue grasping and restraining device of claim 2 wherein said first and second tongue gripping surfaces comprise one or more of the following types of tongue engaging projections or combinations thereof: multiple needle projections, multiple flat triangular projections, multiple blades, multiple frustoconical projections, the tips of multiple staples, and the tips of severed mesh screen.

4. The intraoral tongue grasping and restraining device of claim 2 comprising a lower jaw coupler adapted to couple said second lower support to the lower jaw, and wherein the said at least one biasing member comprises at least one elastic band attached to bias element engaging projections extending outwardly from the upper and lower jaw couplers at a first side of the upper and lower jaw couplers and at least one elastic band attached to bias engaging projections extending outwardly from the upper and lower jaw couplers at a second side of the upper and lower jaw couplers opposite to the first side of the upper and lower jaw couplers.

5. The intraoral tongue grasping and restraining device of claim 1 wherein the tongue engaging projections of at least one of said first and second tongue gripping surfaces are comprised of sharp points that number at least 500 sharp points per square inch.

6. The intraoral tongue grasping and restraining device of claim 5 wherein tongue engaging projections are comprised of sharp points that are 0.05 to 0.1 inch long.

7. The intraoral tongue grasping device of claim 6 wherein the tongue engaging projections have a base with a diameter of 0.02 inch to 0.04 inch.

8. The intraoral tongue grasping and restraining device of claim 1 wherein at least a portion of the first tongue gripping surface is concavely curved in a front-to-back direction.

9. The intraoral tongue grasping and restraining device of claim 1 wherein at least a plurality of the tongue engaging projections of at least one of the first and second tongue gripping surfaces comprise a plurality of staples with their crowns embedded in a base and with their legs projecting outwardly from said base and angled so as to engage the user's tongue at an angle toward the tongue tip.

10. The intraoral tongue grasping and restraining device of claim 1 wherein the upper jaw of the user has upper teeth along each side of the upper jaw and the lower jaw has lower teeth along each side of the lower jaw, further comprising a lower jaw coupler adapted to couple the second lower support to the lower jaw, wherein the lower jaw coupler comprises a lower teeth holding portion configured to engage at least a plurality of teeth along each side of the lower jaw and the upper jaw coupler comprises an upper teeth holding portion configured to engage a plurality of teeth along each side of the upper jaw;
first and second telescoping mechanisms, each of the first and second telescoping mechanisms comprising first and second ends and being coupled at one of the first and second ends to one of the upper and lower teeth holding portions and being coupled at the other of the first and second ends to the other of the upper and lower teeth holding portions,
and wherein each of the first and second telescoping mechanisms comprises a first sleeve portion having a first longitudinal axis, a rod, a second sleeve portion having a second longitudinal axis offset from the first longitudinal axis and an externally threaded support coupler, the first sleeve portion having a rod receiving bore of a non-circular cross-section, the rod being slidably inserted into the first sleeve portion and having at least one flattened surface and a cross-sectional dimension that is sized to engage the rod receiving bore of the first sleeve portion in order to prevent rotation of the rod relative to the first sleeve portion when the rod is slideably engaged by the rod receiving bore, the second sleeve portion comprising an internally threaded portion, the second sleeve portion being mounted to the first sleeve portion, the externally threaded support coupler being threadably engaged with the internally threaded portion of the second sleeve portion, wherein rotation of the second sleeve portion in a first direction around the externally threaded support coupler shifts the first and second sleeve portions axially along the externally threaded support coupler in one direction, and rotation of the second sleeve portion in the opposite direction shifts the first and second sleeve portions axially along the externally threaded support coupler in a direction opposite to said one direction, wherein each of said first and second telescoping mechanisms has a length that is varied by rotating the second sleeve portion around the externally threaded support coupler.

11. A tongue grasping and restraining device for retaining a user's tongue in a forward position during sleep, the user's tongue having a tongue front portion, a tongue tip, a tongue back portion, and filliform papillae, said device comprising:
a first upper support comprising a first base portion and a first tongue gripping surface, and wherein said first tongue gripping surface comprises multiple pointed projections that project from the first base portion and that are sized and positioned to fit between the filliform papillae of the user's tongue to grip the upper surface of the user's tongue, the first base portion having a front and a rear, the front being adapted for positioning toward the tongue front portion, and wherein the pointed projections comprising projections that extend in a direction away from the rear of the first base portion and toward the front of the first base portion,
a second lower support comprising a second base portion and a second tongue gripping surface, and wherein said second tongue gripping surface comprises multiple pointed projections located to grip the lower surface of the tongue of a user,
an upper jaw coupler adapted to couple at least one of said first upper support and second lower support to the upper jaw of the user, and
at least one biasing member operable to urge the first tongue gripping surface toward the second tongue gripping surface with the user's tongue positioned therebetween so as to grasp and restrain the tongue front portion.

12. A device according to claim 11 wherein there are at least five hundred pointed projections per inch.

13. A device according to claim 12 wherein the pointed projections comprise projections that are configured to be angled forwardly toward the tongue tip so as to resist backward sliding of the tongue from between the first tongue gripping surface and the second tongue gripping surface.

14. A device according to claim 11 wherein the pointed projections comprise needles that are angled forwardly toward the tip of a user's tongue so as to resist backward sliding of the user's tongue from between the first tongue gripping surface and the second tongue gripping surface.

15. A device according to claim 11 wherein the at least one biasing member comprises elastic bands coupled to the first upper support and second lower support.

16. A device according to claim 11 wherein the first upper support and second lower support comprise portions of a pouch structure and the at least one biasing member comprises the pouch structure.

17. An intraoral apparatus for grasping and restraining a user's tongue when worn by a user, the user's tongue having a tongue upper surface, a tongue lower surface, a tongue tip, a tongue base, the user having a mouth, an upper jaw and a lower jaw, the apparatus comprising:
a body comprising upper and lower base portions that define at least a portion of a tongue receiving opening therebetween, the upper and lower base portions each comprising a front portion for positioning adjacent to the tongue tip and a rear portion spaced from the front portion, the body also comprising a joining portion coupling the upper and lower base portions together;
a first tongue gripping surface carried by the upper base portion of the body in position to engage the tongue upper surface upon insertion of the user's tongue between the upper and lower base portions;
a second tongue gripping surface carried by the lower base portion in position to engage the tongue lower surface upon insertion of the user's tongue between the upper and lower base portions;
the body comprising a resilient material biasing the upper base portion toward the lower base portion such that the upper and lower base portions are capable of being spread apart so as to permit insertion of the user's tongue between the first and second tongue gripping surfaces and to permit removal of the user's tongue from between the first and second tongue gripping surfaces, and wherein the resilient material comprising the body urges the first and second tongue gripping surfaces toward one another to grip the user's tongue therebetween;
an upper jaw coupler operable to couple the body to the upper jaw when the apparatus is in use; and
wherein at least the first tongue gripping surface comprises a plurality of tongue engaging projections that extend outwardly from the upper base portion and angled toward the front portion of the upper base portion so as to be capable of engaging the tongue upper surface at an angle toward the tongue tip.

18. The apparatus of claim 17 wherein the body comprises a pouch structure with an exterior, and wherein the upper and lower base portions comprise opposing upper and lower portions of the body, the body defining a tongue receiving opening that is generally oval in transverse cross section, wherein the resilient material comprising the body urges the first and second tongue gripping surfaces toward one another so as to be capable of gripping the user's tongue therebetween when the apparatus is worn by a user, and wherein applying inwardly directed opposed side forces to the exterior of said body urges the first and second tongue gripping surfaces away from one another so as to permit the insertion of the user's tongue into the tongue receiving opening and so as to permit the removal of the user's tongue from the tongue receiving opening, and such that removal of the inwardly directed opposed side forces results in the first and second tongue gripping surfaces moving toward one another to grasp the user's tongue therebetween.

19. The apparatus of claim 17 wherein the upper and lower base portions are connected by a flat spring member joining the upper base portion to the lower base portion at a location capable of positioning forwardly of the user's tongue when the apparatus is worn by a user so that the upper base portion and the lower base portion comprise opposing upper and lower portions of a clamp, and wherein upper and lower base portions and flat spring member comprise portions of a monolithic sheet of metal.

20. In a tongue grasping and restraining device for retaining a user's tongue in a forward position when worn by a user, the user's tongue having filliform papillae, a tongue tip, and a tongue upper surface, a tongue engager comprising:
a first support comprising a first base portion and a first tongue gripping surface, and wherein said first tongue gripping surface comprises multiple needle projections projecting outwardly from the first support, the needle projections being sized and positioned and adapted to fit between the filliform papillae of the user's tongue to grip the tongue upper surface; and wherein the needle projections comprise projections that are angled forwardly and are adapted to angle forwardly toward the tongue tip when the device is worn by a user so as to resist backward sliding of the tongue from the first tongue gripping surface.

21. An apparatus according to claim 20 wherein there are at least five hundred needle projections per inch.

22. An apparatus according to claim 20 wherein the user has an upper jaw, the apparatus comprising a jaw coupler coupled to the first support and adapted to couple the first support to the upper jaw.

* * * * *